United States Patent [19]

Hahn et al.

[11] Patent Number: 5,346,814
[45] Date of Patent: Sep. 13, 1994

[54] METHOD OF DETECTING CELL RESPONSE TO CELL-DAMAGING ENERGY

[75] Inventors: George M. Hahn, Stanford; Alie H. Saad, Menlo Park; Amato J. Giaccia, Redwood City, all of Calif.

[73] Assignee: Board of Trustees of the Leland Stanford Jr. University, Stanford, Calif.

[21] Appl. No.: 961,268
[22] Filed: Oct. 14, 1992
[51] Int. Cl.$^5$ .................... C12Q 1/16; G01N 23/00
[52] U.S. Cl. .................... 435/35; 435/968; 436/57; 436/58; 436/59; 436/63; 436/64; 252/600
[58] Field of Search ............ 435/35, 968; 436/57, 436/58, 59, 63, 64; 424/1.1; 252/600

[56] References Cited

PUBLICATIONS

Beilby, M. J., "Potassium Channels and Different States of Chara Plasmalemma," *J. Membrane Biol.* 89: 241–249 (1986).

Kim Yu, A., et al., "Effects of Microwave Radiation on Inducable Ion Transport of Rat Erythrocytes," from *Charge and Field Effects in Biosystems*–2 (Allen, M. J., et al., eds., Plenum Press, New York, 1989) pp. 223–231.

Anderson, et al, *Mol. & Cell. Biol.*, volume 9, No. 8, pp. 3509–3516, 1989.

Carper, S. W., et al., "Biochemical and Cellular Responses to Hyperthermia in Cancer Therapy," UCLA Symposia on Molecular and Cellular Biology vol. 96, pp. 247–256 (1989).

Curran, M. E., et al., "Molecular Cloning, Characterization, and Genomic Localization of a Human Potassium Channel Gene," Genomics 12:729–737 (1992).

Glasgow, G. P., and Purdy, J. A., "External Beam Dosimetry and Treatment Planning," Chapter 9 in *Principles and Practice of Radiation Oncology* (Perez, C. A. et al., eds., J. B. Lippincott Company, Philadelphia, 1992).

Grupe, A., et al., "Cloning and expression of a human voltage-gated potassium channel. A novel member of the RCK potassium channel family," EMBO J. 9(6):1749–1766 (1990).

Hahn, G. M., and van Kersen, I., "Isolation and Initial Characterization of Thermoresistant RIF Tumor Cell Strains," Cancer Res. 48:1803–1807 (1988).

Hahn, G. M., et al., "Survival of Cells Exposed to Anticancer Drugs After Stress," UCLA Symposia on Molecular and Cellular Biology, vol. 96, pp. 223–233 (1989).

Hall, E. J., "Chapter 14: Hyperthermia," in *Radiobiology for the Radiobiologist* (J. B. Lippincott Company, 1988, pp. 293–329).

Hamill, O. P., et al., "Improved Patch–Clamp Techniques for High–Resolution Current Recording from Cells and Cell–Free Membrane Patches," Pflugers Arch. 391:85–100 (1981).

Hoshi, T., et al., "Biophysical and Molecular Mechanisms of Shaker Potassium Channel Inactivation," Science 250:533–538 (1990).

Neher, E., and Sakmann, B., "The Patch Clamp Technique," Scientific American, Mar. 1992, pp. 44–51.

Schmid–Antomarchi et al., *Eur. J. Biochem.*, vol. 142, pp. 1–6, 1984.

Kuin et al., Chemical Abstracts, vol. 114, Ref. #117727f, (Proc. Int. Symp. 1989, 223–31) 1991.

Lee et al., *Proc. Natl. Acad. Sci. USA*, vol. 85, pp. 2019–2023, Mar. 1988.

Beilby, Biological Abstracts, vol. 82(1), Ref. #1853, 1986 (J. Membr. Biol. 89(3):241–250, 1986).

Lew et al., Biological Abstracts, vol. 89(11), Ref. #119739, 1990 (Plant Physiol. C Bethesda) 92(3):822–830, 1990).

Ramaswami et al., Biological Abstracts, vol. 93(2): Ref. #16875, 1990 (Mol. Cell. Neurosci 1(3):214–223, 1990).

Pahapill et al., Chemical Abstract, vol. 112, Ref. #137274t, 1990 (J. Physiol. (London) 1990, 422, 103–26).

Saad et al., *Proc. Natl. Acad. Sci. USA*, vol. 89, pp. 9396–9399, Oct. 1992.

*Primary Examiner*—Michael G. Wityshyn
*Assistant Examiner*—Abdel A. Mohamed
*Attorney, Agent, or Firm*—Peter J. Dehlinger; Carol A. Stratford; Vincent M. Powers

[57] ABSTRACT

A method of assessing a cell's susceptibility to cell-damaging energy, such as ionizing radiation and heat, is disclosed. The method is based on measurable changes in voltage-dependent potassium channel currents in the cell in response to the energy. Also disclosed is a method for screening drugs which are effective to sensitize a cell to cell-damaging radiation.

17 Claims, 16 Drawing Sheets

Fig. 5

Fig. 10
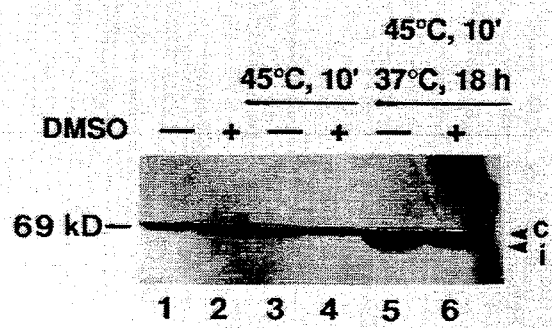
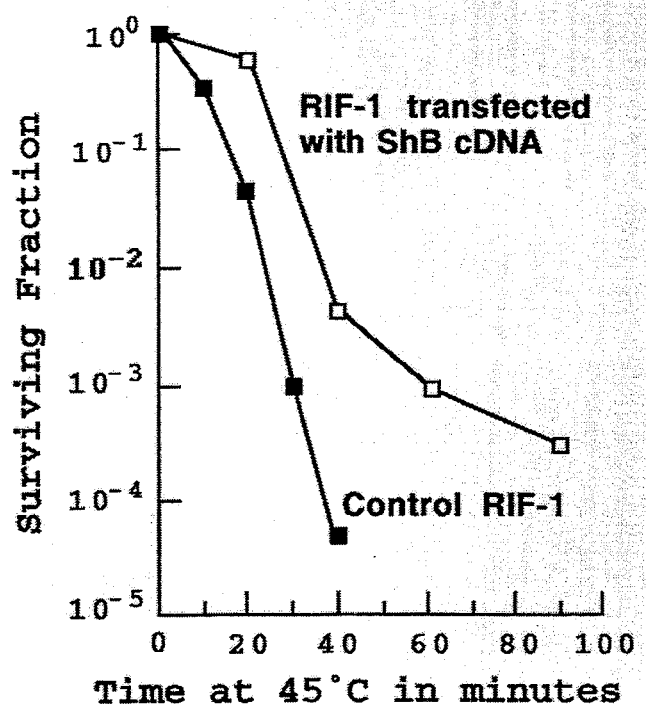
Fig. 11

Fig. 12
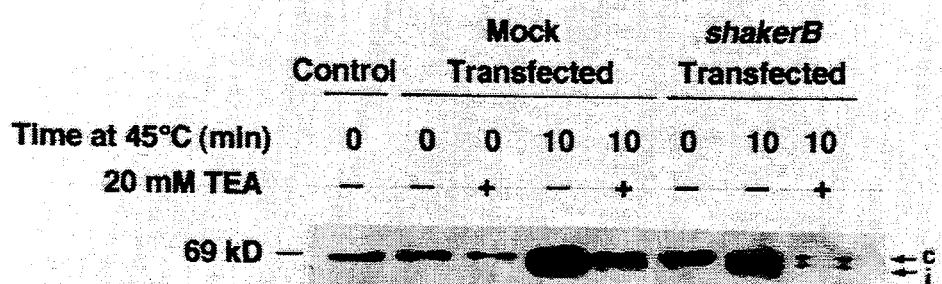
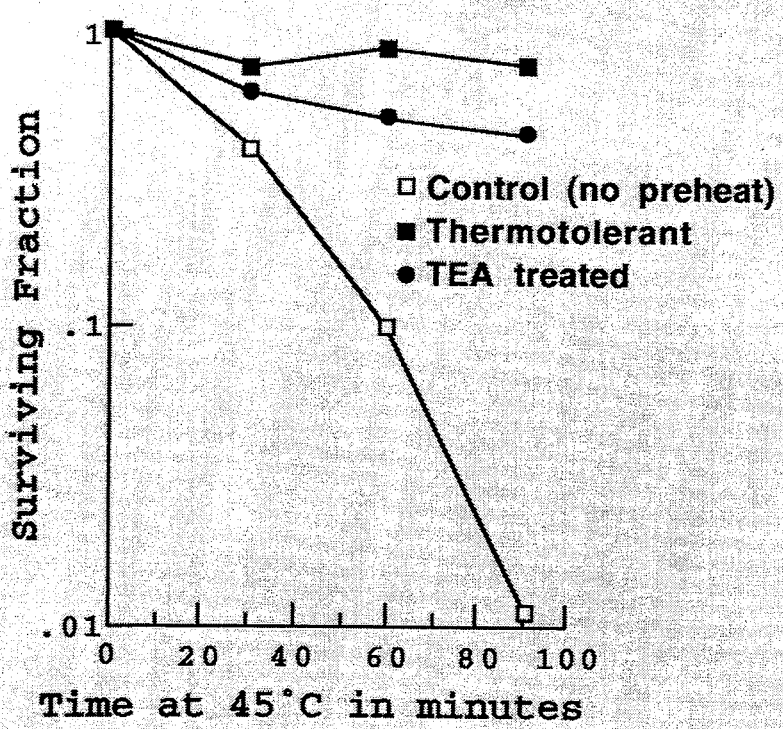
Fig. 13

Fig. 20

PRIMERS:

FORWARD: C A G G C C T C C A T G A G G G A G C T G G G G G

REVERSE: C G A T G G C A C A C A G C G A G C C C A C

Fig. 21

AG8 CAGGCCTCCATGAGGGAGCTGGGGCTGCTCATCTTCTTCCTCTTCATCGG
K1  CAGGCCTCCATGAGGGAGCTGGGGCTGCTCATCTTCCTCTTCCTTCATCGG

AG8 GGTCATCCTCTTCTCCAGTGCCGTCTACTTCGCAGAGGCTGACAACCAGG
K1  GGTCATCCTCTTCTCCAGTGCCGTCTACTTCGCAGAGGCTGACAACCAGG

AG8 GAACCCATTTCTCTAGCATCCCTGACGCCTTCTGGTGGG
K1  GAACCCATTTCTCTAGCATCCCTGACGCCTTCTGGTGGG

METHOD OF DETECTING CELL RESPONSE TO CELL-DAMAGING ENERGY

Portions of the research conducted in support of the present invention were sponsored by the National Cancer Institute, National Institutes of Health, Grants CA-3353, CA-19386, CA-32827, and CA-44665.

1. FIELD OF THE INVENTION

The present invention relates to methods for detecting exposure of cells to cell-damaging energy, particularly heat or ionizing radiation.

2. REFERENCES

Anderson et al. (1989) Mol. Cell. Biol. 9:3509–3516.

Armstrong, C. M., and Bezanilla, F. (1974) J. Gen. Physiol. 63:533–552.

Ausubel, F. M. et al. (1992) *Current Protocols in Molecular Biology*, John Wiley and Sons, Media, Pa.

Carper et al. (1989) "Biochemical and Cellular Responses to Hyperthermia in Cancer Therapy" in Stress-Induced Proteins, M. L. Pardue et al., eds, Alan R. Liss, Inc., New York, pp. 247–256.

Grupe, A. et al. (1990) EMBO J. 9:11749–1756.

Hahn, G. M., and van Kersen, I. (1988) Cancer Res. 48:11803–1807.

Hahn et al. (1989) "" in Stress-Induced Proteins, M. L. Pardue et al., eds, Alan R. Liss, Inc., New York, pp. 223–233.

Hamill, O. P., et al. (1981) Pflugers Arch. 391:85–100.

Hille, B. (1992) *Ionic Channels of Excitable Membranes*, 2nd Ed., Sinauer Associates Inc., Sunderland, Mass.

Neher, E., and Sakmann, B. (1992) 37 The Patch Clamp Technique" in Scientific American, March, 1992, pp. 44–51.

Riabowl, K. T., et al (1988) Science 242:433–436.

Sanger, F. et al. (1977) Proc. Natl. Acad. Sci. USA 74:5463–5467.

Schreck, R., Rieber, P., and Baeuerle, P. A. (1991) EMBO 10:2247–2258.

Schwarz, T. L., et al. (1990) Drosophila Neuron 2:119–127.

Zimarino, V., and Wu, C. (1987) Nature 327:727–730.

BACKGROUND OF THE INVENTION

Radiation therapy (e.g., x-ray irradiation) is a widely used modality for treating cancer cells. Various protocols have been developed to treat a number of specific neoplastic conditions. These methods are based in part on selective killing of rapidly dividing cells.

Another modality for treating cancer cells is hyperthermia. By heating a target area, e.g., by use of focussed microwave radiation, ultrasound, or radiofrequency, cells can be selectively injured or killed at a solid-tumor site. Success of this type of therapy can depend in part on the poorer vascularization of some solid tumors, and therefore, the poorer ability of such cells to dissipate heat.

It is known that patients vary widely in their response to cell-damaging radiation, i.e., irradiation treatment and hyperthermic treatment. An important consideration is the ability of target cells to develop resistance, either rapidly or over an extended treatment time, to the cell-damaging energy. Hyperthermic treatment, for example, can induce heat-shock proteins that appear to protect cells from heat, possibly by preventing heat denaturation of other cellular proteins.

Because target cells can vary in their short-and long-term responses to radiation or hyperthermic treatment, it is desirable to assess the susceptibility of target cells to such treatments before treatment is initiated. Such an assessment can be useful in selecting a therapeutic regimen suited to the particular properties of the target cells.

SUMMARY OF THE INVENTION

The present invention includes, in one aspect, a method of assessing the susceptibility of a cell of a known origin to cell-damaging energy. The method includes exposing the cell to a selected amount of such energy, and measuring a voltage-dependent potassium current in a cell of such origin. The change in the measured current before and after exposure to the energy is used to assess the ability of a cell of such origin to resist said energy.

In one general embodiment, the cell-damaging energy is ionizing radiation, and the exposure can be by irradiating the cells with $\gamma$- or x-radiation, or by contacting the cells with a high-energy radiation emitter, over a selected exposure period.

In another general embodiment, the cell-damaging energy is heat, and the exposure is by heating the cells, e.g., by microwave irradiation or temperature increase, over a selected heating period.

The method is used, for example, in assessing cancer cells in a human patient for their susceptibility to radiation or heat, in determining optimal treatment strategies.

Also disclosed is a method for screening compounds which are effective to sensitize tumor cells to cell-damaging energy. The method includes incubating a test compound with a cultured cell that exhibits an inducible voltage-dependent potassium current upon exposure to cell-damaging energy, exposing the cell to a selected level of the cell-damaging energy during the incubation, and measuring the voltage-dependent potassium current in the cell, before and after such exposure to the cell-damaging energy. The change in voltage-dependent potassium current measured after exposure to the energy is used as an indicator of the test compound's ability to block induction of increased potassium currents in response to exposure to cell-damaging energy.

These and other objects and features of the invention will become more fully apparent when the following detailed description of the invention is read in conjunction with the accompanying drawings.

BRIEF DESCRIPTION OF THE DRAWINGS

FIG. 5 shows a Western blot to assess levels of potassium channel proteins in RIF-1 and TR-4 cell lysates following cell growth at 45° C. Potassium channel proteins were detected using an antibody (ShA-3) immunoreactive with ShakerB potassium channel proteins. Lane 1: molecular weight markers; lane 2: RIF-1 cell lysate; lane 3: TR-4 cell lysate;

FIG. 10 shows a Western blot to assess HSP70 polypeptide levels in RIF-1 cells grown for 7 days in the presence or absence of DMSO. Following day 7 of growth, the cells were heated at 45° C. for 10 min, and were either loaded immediately on an SDS polyacrylamide gel for analysis, or were loaded on the gel after an additional 18 hour growth period at 37° C. to allow synthesis of heat-inducible HSP70 polypeptides. HSP70 polypeptides were detected using an antibody (N-27) that recognizes both the constitutive (c) and inducible (i) forms of HSP70. These forms are designated in the figure as "c" and "i", respectively;

FIG. 11 illustrates the heat resistance of RIF-1 cells transfected with a vector containing a gene encoding a ShakerB polypeptide, with data for mock-transfected RIF-1 cells (no plasmid during transfection procedure) shown for comparison. Following transfection, the cells were grown at 37° C. for 2 days to allow expression of the Shaker proteins. The cells were then heated and assayed for survival as in FIG. 4 above;

FIG. 12 shows a Western blot to characterize the heat-inducibility of HSP70 polypeptides in the control and ShakerB plasmid-transfected RIF-1 cells described above for FIG. 11. Cells were heated for 10 min at 45° C. in the presence or absence of 20 mM TEA and then grown for an additional 18 hours in the absence of TEA to allow induction of HSP70 polypeptides. The HSP70 polypeptides were detected as in FIG. 10;

FIG. 13 shows the effect of TEA on the development of thermotolerance in TR-4 cells. Cells were made thermotolerant by heating the cells at 45° C. for 40 min, followed by incubation at 37° C. for 12 h, where 20 mM TEA was present or absent during the heating and/or incubation steps. Heat resistance was then assessed as described above for FIG. 4 (open squares, control group (no heat treatment); solid squares, TEA absent from procedure; solid circles, 20 mM TEA present during heat step and subsequent incubation step).

FIG. 20 shows two suitable oligonucleotide primers for use in isolating a voltage-dependent potassium channel gene (both shown 5' to 3'): forward oligonucleotide primer: SEQ ID NO: 1; reverse oligonucleotide primer: SEQ ID NO: 2.

FIG. 21 shows a partial sequence of a clone (AG8, SEQ ID NO: 3) obtained using the primers shown in FIG. 20. Also shown for comparison is the corresponding sequence from the gene for human voltage-gated potassium channel K1 (SEQ ID NO: 4).

DETAILED DESCRIPTION OF THE INVENTION

I. Definitions

Figure 1A:
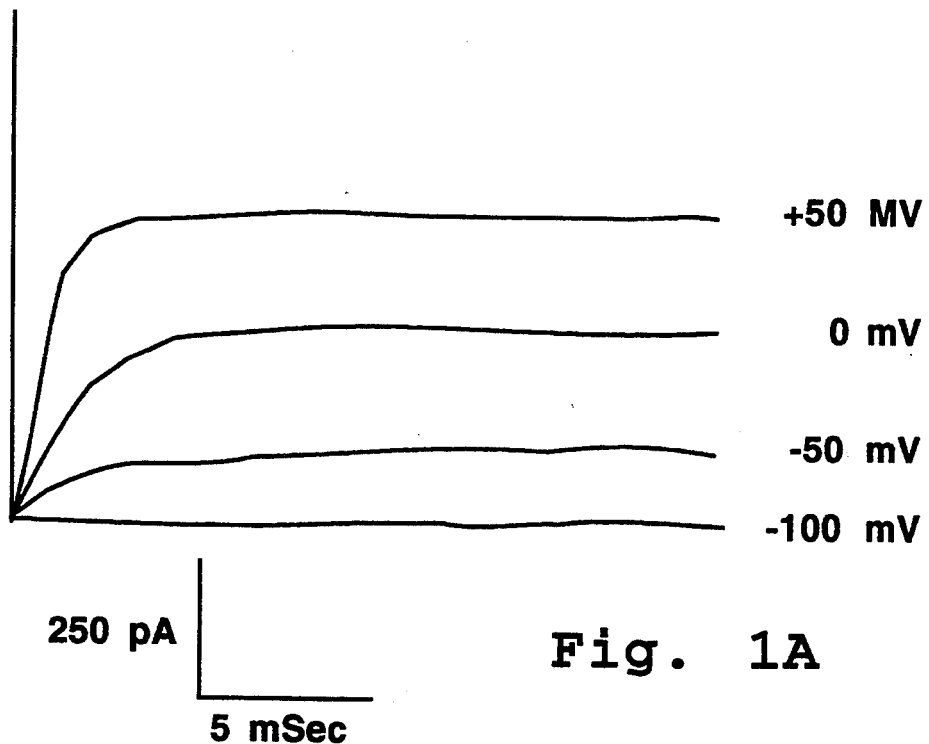
FIGS. 1A and 1B show voltage-dependent potassium channel currents induced in TR-4 cells (1A) and RIF-1 cells (1B) following heating of the cells at 45° C. for 10 minutes.

The terms defined below will have the following meaning, unless otherwise stated:

"Cell-damaging energy" means ionizing radiation or heat at a level and over an exposure period sufficient to damage cells, as evidenced by cell death, cell toxicity, or inhibition of cell growth or metabolism relative to cell growth or metabolism in the absence of such energy. Inhibition of cell growth or metabolism may be evidenced, for example, by reduced incorporation of amino acids into cellular proteins, or of nucleotides into cellular polynucleotides.

"Ionizing radiation" includes electromagnetic radiation having a wavelength in the range from about 400 nm (4000 Å) to about 0.1 pm (0.001 Å). Ionizing radiation includes ultraviolet light (~400 nm to ~10 nm), x-rays (~10 nm to ~10 pm), and gamma-rays (~10 pm to ~0.1 pm). For the purposes of the invention, "ionizing radiation" refers particularly to those types of ionizing radiation used in cancer therapy.

In general, the dose of ionizing radiation absorbed by a sample can be expressed in units of rad or Gray. A rad, which is equal to 1 cGy (centigray), is equal to 100 ergs per gram of sample (i.e., an amount of energy imparted to the sample per sample unit mass).

"Cell heating" or "exposing cells to heat" is defined herein as elevating the temperature of a cell, either by localized heating, e.g., that which may be produced by a focused microwave beam, or by generalized heating, e.g., by a temperature bath.

Membrane voltage potentials are defined as the electrical potential of the inside of the cell minus that of the outside of the cell.

II. Potassium Channel Currents

An important feature of the invention, discussed below, is the discovery that (i) one of the cellular responses to cell-damaging energy involves cellular potassium channel activity, and (ii) this activity manifests itself as a measurable increase in voltage-dependent potassium channel currents.

Typically, voltage-dependent potassium channel currents are due to the efflux of potassium ions from a cell in response to a potential difference applied across the cellular membrane. The voltage is applied typically by a microelectrode. When a threshold voltage is reached, the channel opens, allowing movement of potassium ions through the channel.

Voltage-dependent potassium channel current can be measured using conventional electrophysiological techniques (e.g., see Neher et al., 1992). In one method, the current is measured by whole-cell recording using the voltage-clamp method of Hamill et al. (1981). A cell is tightly affixed by suction to a microelectrode pipette tip to establish a tight pipette-membrane seal. Following seal formation, the membrane patch around which the seal has been formed is disrupted by either a voltage pulse, or more usually, by a pulse of suction, thereby allowing whole-cell current recording. Preferably, the microelectrode contains a solution that mimics the ionic interior of the cell (e.g., a buffer containing Ca, EGTA, and a high K+ concentration; Hamill et al., 1981).

Figure 1B:
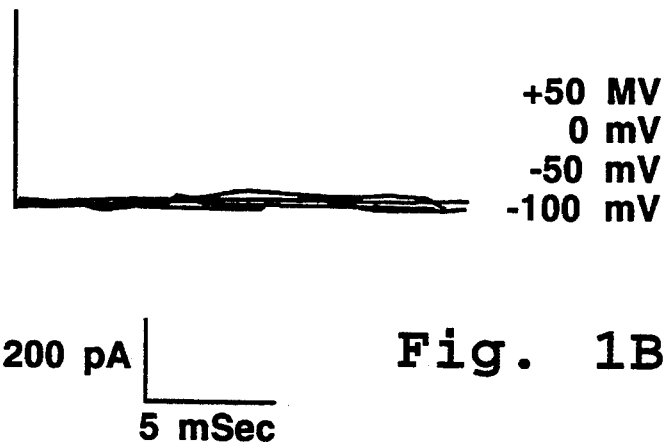
Figure 2:
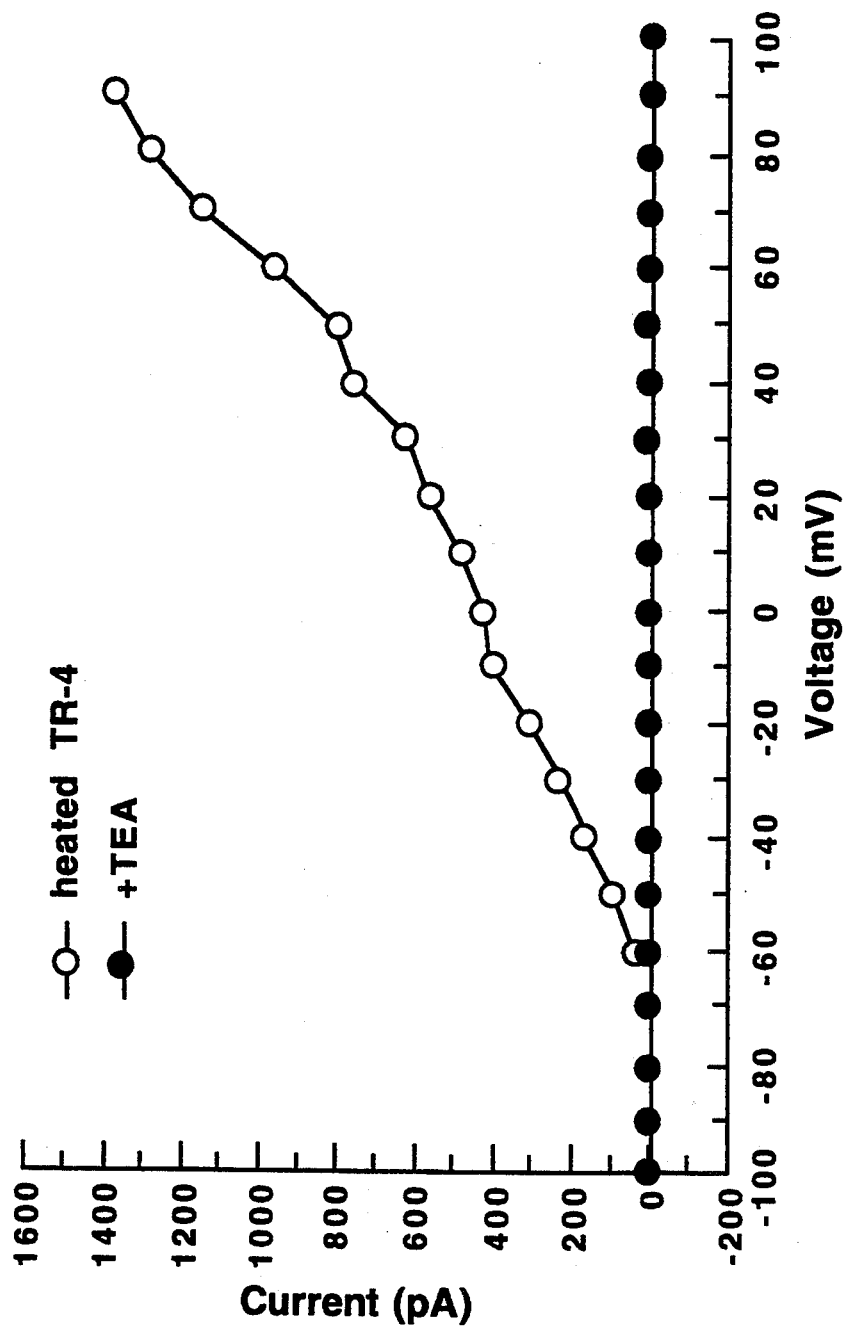
FIG. 2 illustrates the inhibition of heat-induced potassium channel currents by 20 mM tetraethylammonium ions (TEA)

Examples I and 2 illustrate specific protocols which are suitable for use in the invention for measuring voltage-dependent potassium currents. Briefly, a voltage clamp protocol is performed in which the cell potential is stepped from a holding potential of about −75 mV to a prepulse voltage of −120 mV for 500 msec, followed by stepping to test potentials ranging from about −100 mV to 100 mV. Representative I-V (current-voltage) plots obtained with selected cells are shown in FIGS. 1A, 1B, and 2.

To verify that the measured current is a potassium channel current, the effects of selective potassium channel blocking agents can be examined. Blocking agents that selectively inhibit potassium channel currents when administered extracellularly include tetraethylammonium (TEA) and Cs+ ions (Hille, 1991). Use of such a blocking agent is illustrated in Example 2 and FIG. 2.

Tail current measurements provide a second means of distinguishing a potassium channel current from a non-potassium ion current. As detailed in Example 3, tail currents are used to determine the reversal potential of the voltage-dependent current for a range of extracellular potassium concentrations. A linear dependence of reversal potential on $\ln([K+]_{ext}/[K+]_{int})$ (in accord with the Nernst equation) is strong evidence that the observed currents are voltage-dependent potassium channel currents.

In accordance with another aspect of the invention, it may be useful to assess the levels of voltage-dependent potassium channel proteins (VDPCs) in a selected cell sample. Western blot methods are well known and afford a convenient means for assessing VDPC levels. An exemplary procedure is described under Materials and Methods in the Examples section below, with specific applications described in Examples 5 and 9.

II. Induction of potassium Currents by Cell-Damaging Energy

In one aspect, the invention is a method of assessing the susceptibility of a cell of a known origin to cell-damaging energy. The method includes exposing the cell to a selected amount of cell-damaging energy, and measuring a voltage-dependent potassium current in the cell before and after said exposing. The change in the measured currents before and after exposure is used to assess the ability of the cell to resist such energy.

A. Cellular Response to Heat

In this embodiment of the invention, the cell is exposed to a selected level of heating, by which is meant an amount of heat sufficient to raise the cell to a selected elevated temperature over a given heat-exposure time. The heat may be applied by irradiating the cells with microwave radiation, from a suitable microwave source, or by thermal heating, e.g., placing the cell medium in contact with a higher-temperature source. Typically, in the latter case, the cell and its medium is raised to a temperature of between about 40°–45° C., for about 1–45 minutes.

Prior to and following exposure of the cell to heat, the potassium current of the cell is measured, to determine the short term response of the cell to the energy stimulus. The change in current indicates the extent to which the cells are resistant to the damaging stimulus.

Example 1 describes a study comparing the potassium current activities of the heat-resistant cell line, TR-4 (Hahn and van Kersen, 1988), and the murine tumor cell line, RIF-1, from which the TR-4 cells were derived. Following overnight growth at 37° C., cells were heated in a 45° C. water bath for 10 minutes, and then returned to 37° C. No currents could be detected with either cell line in the absence of the heat treatment. However, as shown in FIG. 1A, TR-4 cells exhibited voltage-dependent currents. When the heat-induced currents in TR-4 cells were monitored for several hours following heat treatment, both fast-inactivating and delayed-rectifier currents were observed. The currents gradually subsided and were no longer detectable after about 6 hours. In contrast, RIF-1 cells exhibited no detectable currents, even at a voltage potential of 50 mV (FIG. 1B), although small currents (e.g., ~100 pA at 0 mV) could be observed with RIF-1 cells during (but not after) heating.

Figure 3:
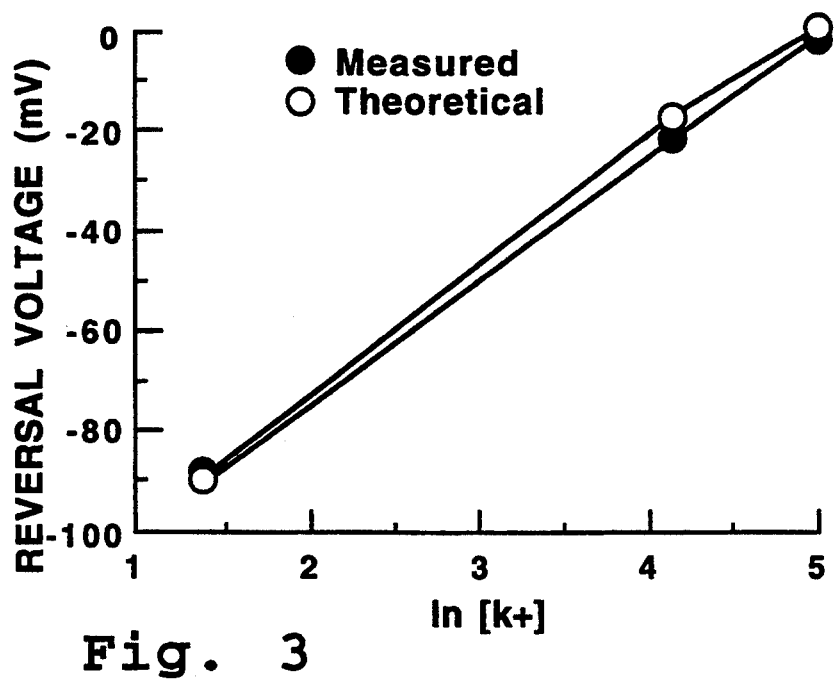
FIG. 3 shows the correlation of reversal potentials with the log of the external potassium ion concentration ($\ln([K+]_{ext}/[K+]_{int})$) measured in TR-4 cells following heating at 45° C. for 30 minutes.

That the voltage-dependent currents exhibited by the TR-4 cells were indeed potassium ion currents was demonstrated by use of the K+ channel blocker, tetraethylammonium (TEA), and also by reversal potential measurements. As detailed in Example 2 and illustrated in FIG. 2, including 20 mM TEA in the cell medium during current measurement following heat treatment abolished nearly all detectable current. Moreover, as shown in FIG. 3 (see Example 3), the reversal potential of the currents showed a linear correlation with $\ln([K+]_{ext}/[K+]_{int})$ indicating the currents were due to potassium ion currents.

Figure 4:
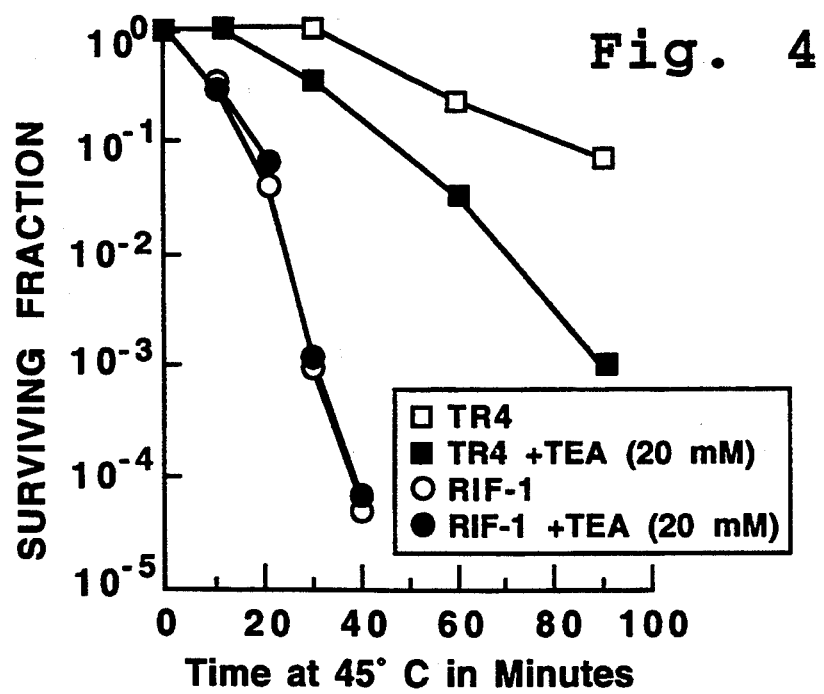
FIG. 4 shows the effect of 20 mM TEA on the survival fraction of TR-4 and RIF-1 cells following heating of the cells at 45° C. for various durations. Survival fractions were determined by clonogenic assay.

The effect of TEA on the survival of TR-4 and RIF-1 cells following heat treatment is illustrated in FIG. 4. Cells were heated at 45° C. for various lengths of time in the presence or absence of 20 mM TEA, and cell survival was assessed by clonogenic assay, as detailed in Example 4. As can be seen from FIG. 4, the TR-4 cells were substantially more heat-resistant than RIF-1 cells, regardless of the presence of TEA. However, whereas TEA had no effect on the survival rate of RIF-1 cells, it had a significant effect on the survival rate of TR-4 cells for heating times longer than about 20 minutes. These results suggest that the heat-induced potassium currents observed in TR-4 cells play a role in protecting the cells from heat.

To examine whether the differences in heat resistance might be due to differential expression of potassium Channels, lysates of RIF-1 and TR-4 cells that had not been heat-treated were electrophoresed in SDS-polyacrylamide denaturing gels and examined by Western blot analysis. Potassium channel proteins were detected using the antibody, ShA-3, a polyclonal rabbit antibody that recognizes ShakerB K+ channel proteins (Schwarz et al., 1990).

Figure 5:
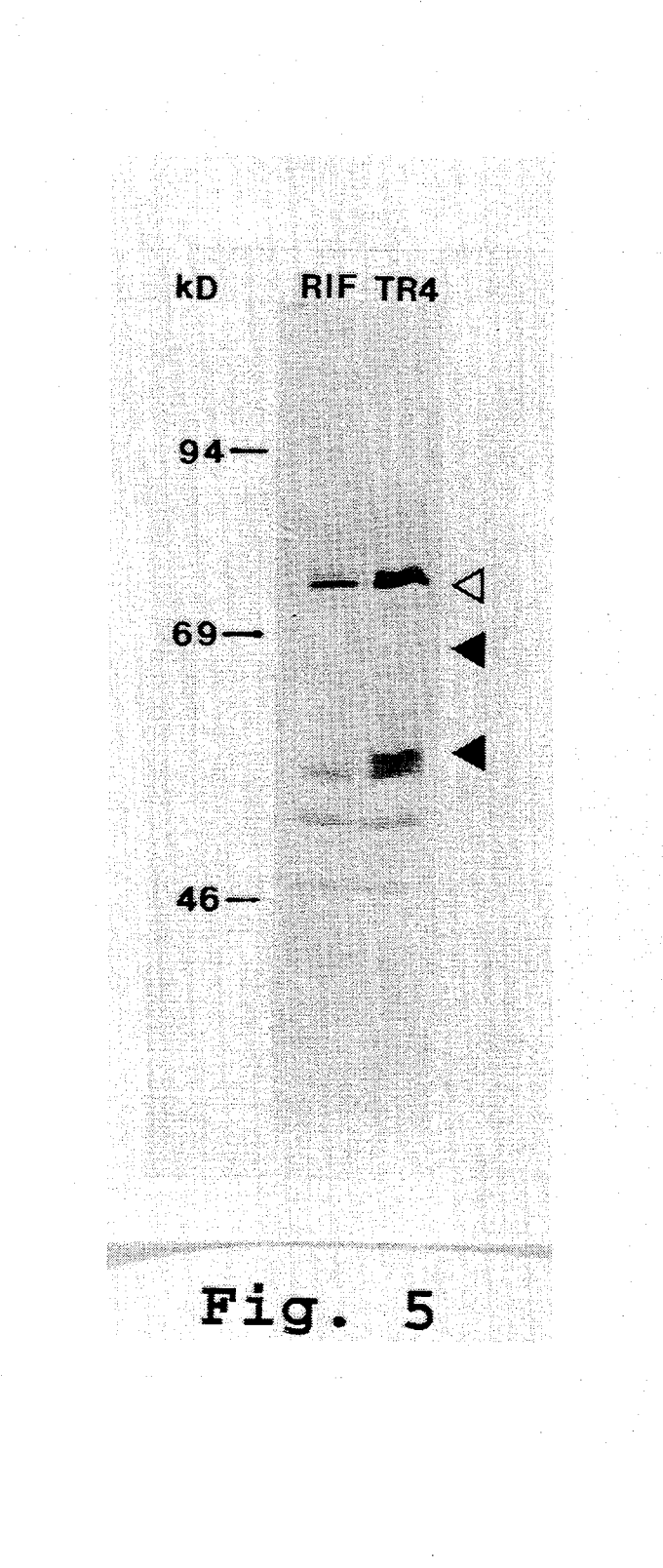

As shown in FIG. 5, the TR-4 cells contain at least two polypeptides that are recognized by the polyclonal antibody ShA-3 and that are not present in the RIF-1 cells (61 kD and 66 kD, indicated by solid arrows). In addition, at least one polypeptide is expressed at a higher level in the TR-4 cells (74 kD, indicated by open arrow). Note that the molecular weight of the 74 kD polypeptide is consistent with that reported for the ShakerB K+ channel protein (Schwarz et al., 1990). These results suggest that heat resistance in TR-4 cells is mediated at least in part by potassium channel proteins that are present in the membranes of TR-4 cells and that can be activated by heat.

Example 6 describes a study on the effects of heat-induced potassium currents on the activation of heat-shock factor (HSF). TR-4 and RIF-1 cells were heated at 45° C. for 15–40 minutes in the presence or absence of 20 mM TEA, and the level of HSF activation in the cells was assessed using a gel retardation assay (Zimarino et al., 1987). In the assay, the level of activated HSF could be assessed by the appearance of a complex of HSF with its DNA recognition sequence (the heat shock element, HSE).

Figure 6:
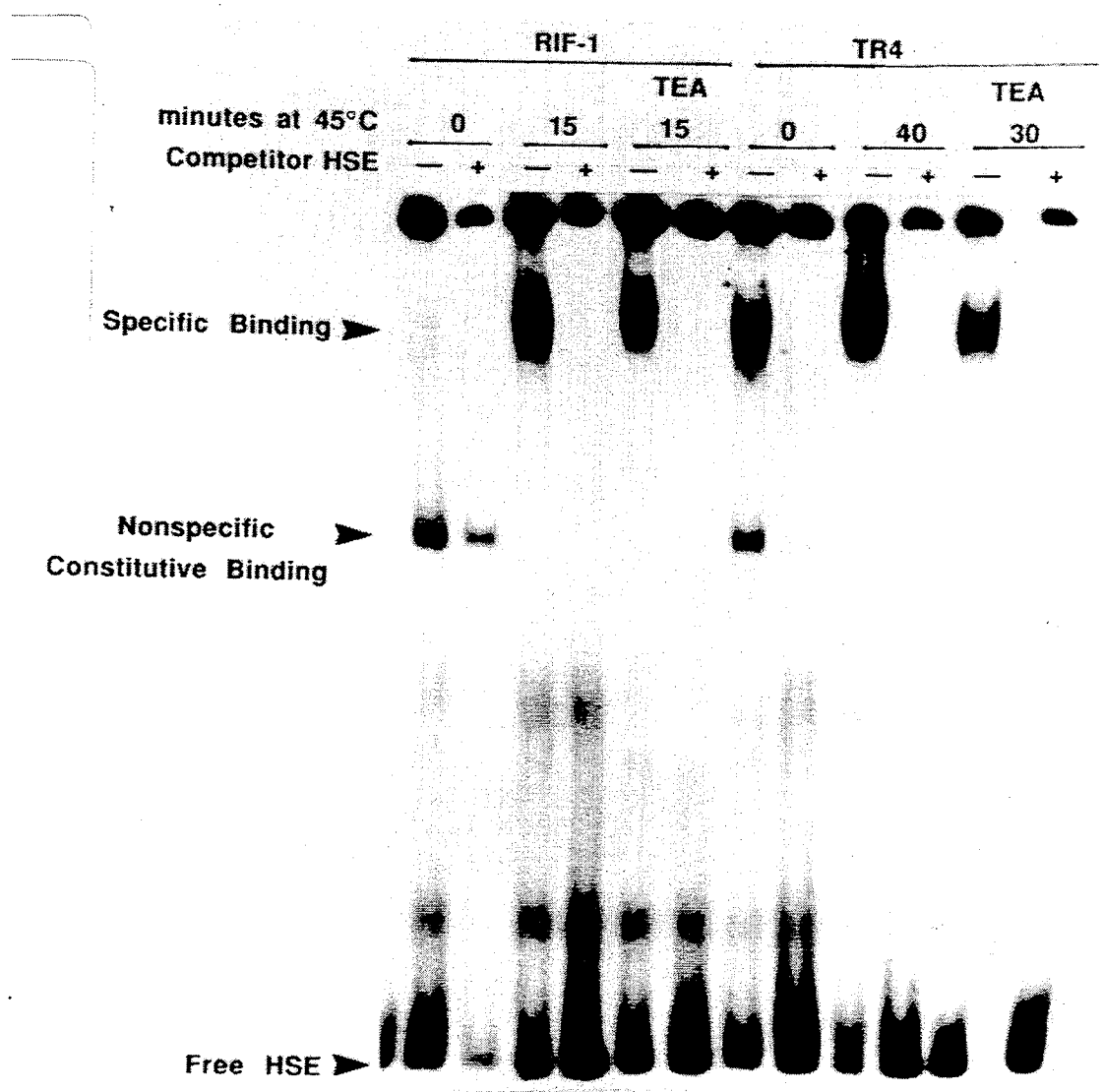
FIG. 6 illustrates an autoradiogram obtained from a gel retardation assay to measure the effects of TEA on the activation of heat shock factor (HSF) in RIF-1 and TR-4 cells. Cells were heated at 45° C. for 15–45 minutes prior to assay. The presence or absence of 20 mM TEA is indicated above each lane; the absence or presence of cold competitor HSE (heat shock element) oligonucleotide is denoted by "−" or "+", respectively.

As seen from FIG. 6, the presence of TEA during heating eliminated most or all of the heat-induced activation of HSF in TR-4 cells, although a constitutive level of activated HSF remained. In contrast, TEA had no effect on the levels of activated HSF in RIF-1 cells.

From these results it appears that the heat-induced K+ currents in TR-4 cells correlate with HSF activation.

In further experiments in support of the present invention (Example 11), RIF-1 cells were transfected by electroporation with a plasmid containing the ShakerB gene. As a control, a separate set of cells were mock-transfected in the absence of the plasmid. Following the transfection procedure, the cells were incubated for another 2 days to allow expression of the transfected gene prior to heat and TEA experiments. To examine the effects of transfection, cells were heated at 45° C. for various times (0–100 min) and then plated to determine survival fraction. FIG. 11 shows that the transfected cells were more heat-resistant than the control, mock-transfected cells.

In a parallel set of experiments, heating of the mock- and plasmid-transfected cells was performed in the presence or absence of 20 mM TEA, and the expression of HSP70 proteins was determined by immunoblot analysis (described in Example 11). As seen from FIG. 12, the inhibitory effect of TEA on expression of HSP70 (both the constitutive (c) and inducible (i) forms) was greater in the cells transfected with the ShakerB gene than in the mock-transfected cells. This result shows that inhibition of HSP70 expression in TR-4 cells by TEA correlates with an increased level of voltage-dependent potassium channels in these cells.

TR-4 cells can be rendered "theremotolerant" by heating at 45° C. for 40 min, followed by a 12 h incubation at 37° C. This general phenomenon has been observed with many other cells and is characterized by a temporary enhancement in resistance to heat that develops several hours after exposure to a "priming" heat dose and then subsides several hours or days later (Hahn et al., 1989; Carper et al., 1989).

To determine whether the inhibitory effect of TEA on the heat-induced currents in TR-4 cells noted above (see also Example 2) could extend as well to inhibiting the development of thermotolerance in these cells, TR-4 cells were heated for 40 minutes at 45° C., followed by incubation at 37° C. for 12 hours to allow thermotolerance to develop. Following these two steps, the cells were assessed for survival by clonogenic assay. TEA (20 mM) was present in the medium during either or both of the heating and incubation steps of protocol, as detailed in Example 12. As can be seen from FIG. 13, TR-4 cells that had not been subjected to the 40 minute heat treatment were much less heat-resistant than the cells that had been heated and then incubated at 37° C. for 12 hours. In addition, the presence of 20 mM TEA during either or both steps of the protocol (i.e., the 45° C. heating step or the 12 hour incubation step) had little effect on the development of thermotolerance by the cells.

Other experiments have shown that exposure of A549 cells to microwave energy or ultrasound can also induce voltage-dependent potassium currents.

B. Cellular Response to Ionizing Radiation

In this embodiment of the invention, the cell is exposed to a selected dose of ionizing radiation, by which is meant a selected radiation level, measured in centigrays (or rad), over a selected exposure period. The radiation source can be an x- or γ-ray emitter, or a β-emitter, for example, according to the needs of the clinician or experimentalist. Prior to and after exposure to the selected radiation dose, the voltage-dependent potassium current of the cell is measured. The change in current following exposure to the radiation dose indicates the extent to which the cells are resistant to the selected form of ionizing radiation.

Figure 14A:
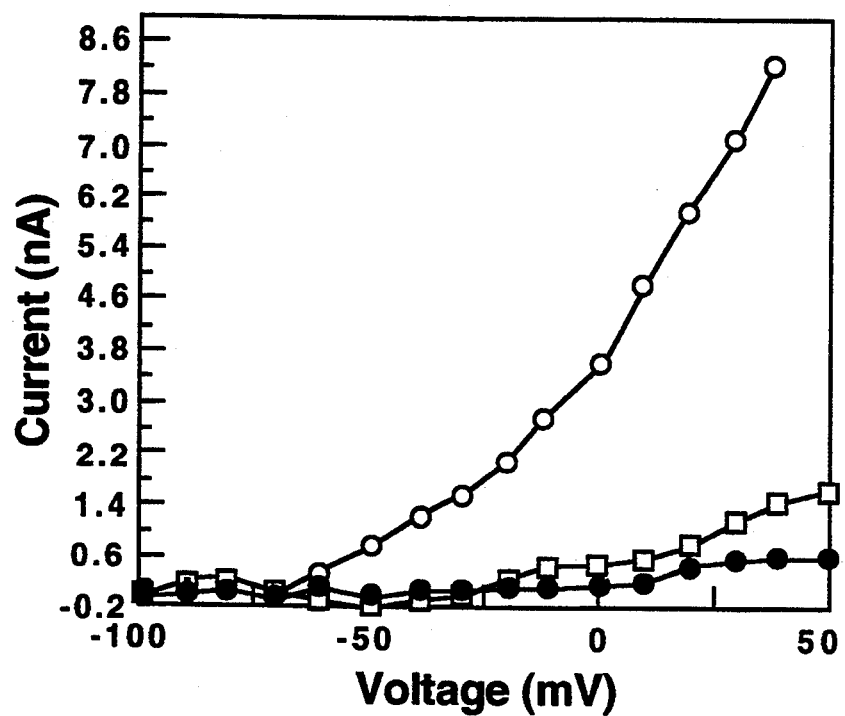
FIG. 14A illustrates voltage-dependent potassium currents induced by treating A549 cells with various doses (cGy) of $^{137}Cs$ γ-irradiation: open circles, 150 cGy; open squares, 10 cGy; solid circles, 0 cGy.

Example 13 describes a study in which A549 cells (a well-characterized human lung carcinoma cell-line) were exposed to moderate doses of $^{137}$Cs radiation, and then voltage-dependent potassium currents induced in the cells were measured. The observed currents, measured within 20 minutes of irradiation, are shown in FIG. 14A. As can be seen, irradiation with 10 cGy (open squares) produced K+ currents that were readily distinguishable from the low background current exhibited by the control cells (solid circles). Substantially higher currents were induced with a 150 cGy exposure (open circles).

Figure 14B:
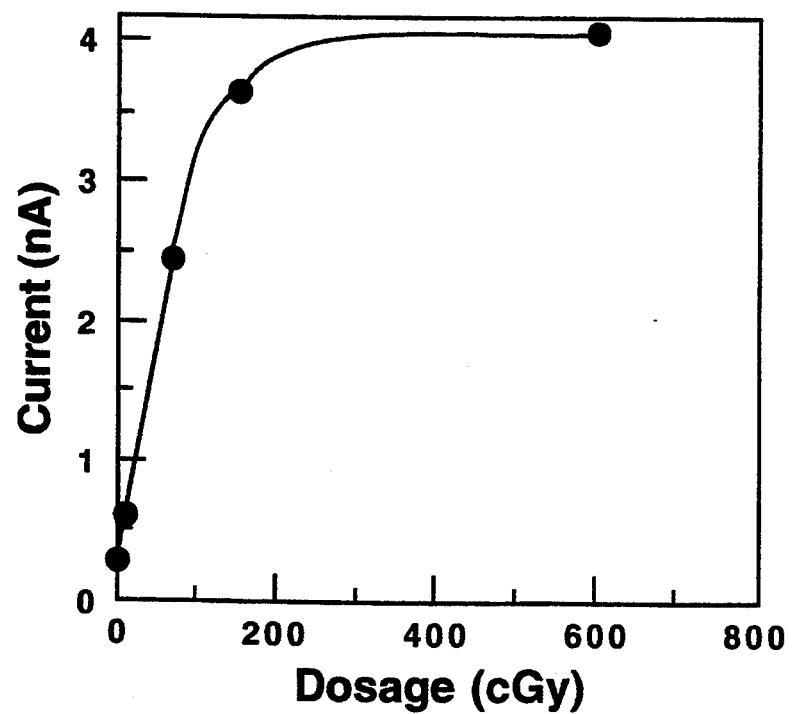
FIG. 14B shows levels, recorded at 0 mV, of voltage-dependent potassium currents measured for dosages ranging from 10 to 600 cGy.

FIG. 14B shows a plot of radiation-induced currents (measured at 0 mV) versus radiation dose. As can be seen, for exposures between 0 and about 150 cGy, the magnitude of the induced current appears to correlate linearly with radiation dosage. The current induced by 600 cGy was not much greater than that induced by 150 cGy.

Figure 14C:
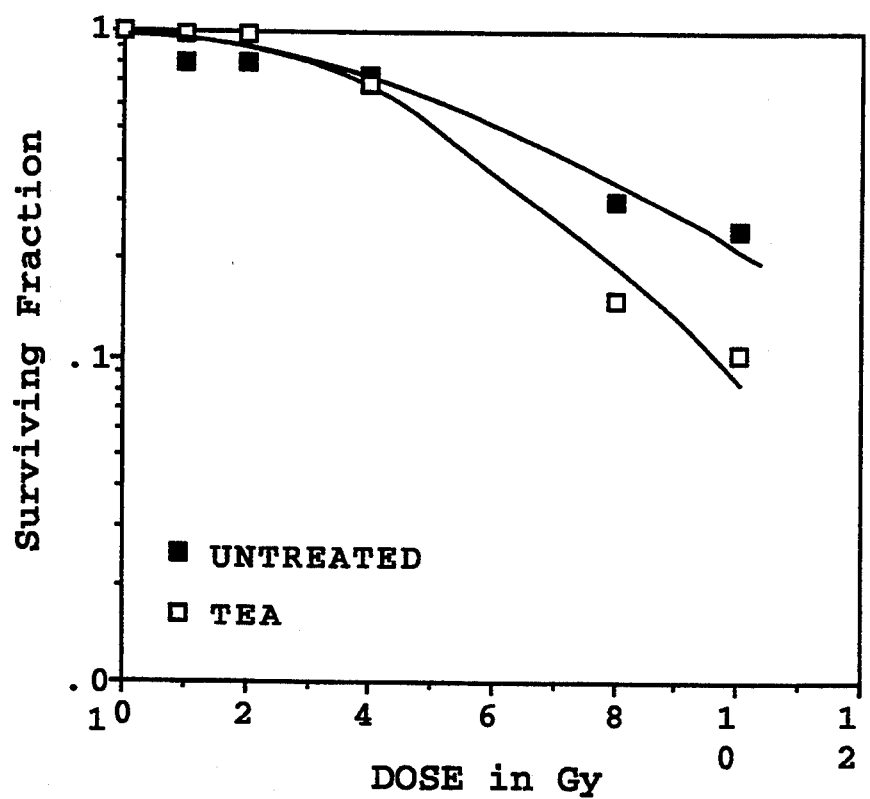
FIG. 14C shows the survival rate of A549 cells treated with $^{137}Cs$ radiation doses ranging from 0 to 10 cGy, Wherein 20 mM TEA was present or absent in the cell medium during irradiation of the cells.

FIG. 14C shows the survival rate of A549 cells as a function of $^{137}$Cs radiation dosage, where irradiation was performed in the presence and absence of 20 mM TEA in the cell medium. As can be seen, doses up to about 200 cGy caused little or no cytotoxicity, when assessed by clonogenic assay. At doses greater than about 200 cGy, cytotoxicity was increased somewhat when TEA was present during irradiation.

Figure 15A:
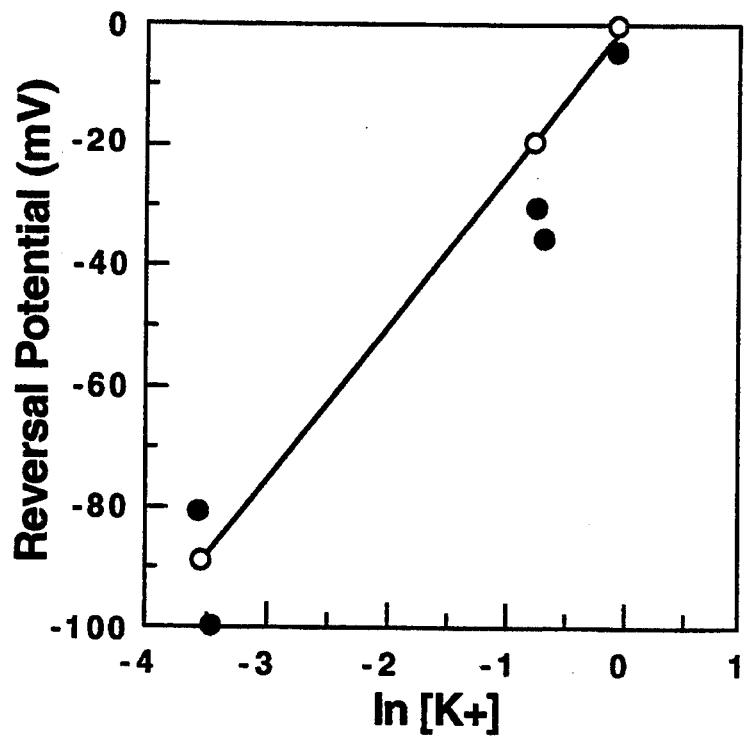
FIGS. 15A shows the correlation between observed (solid circles) and theoretical (open circles) reversal potentials for radiation-induced (150 cGy, $^{137}CS$) potassium currents in A549 cells.
Figure 15B:
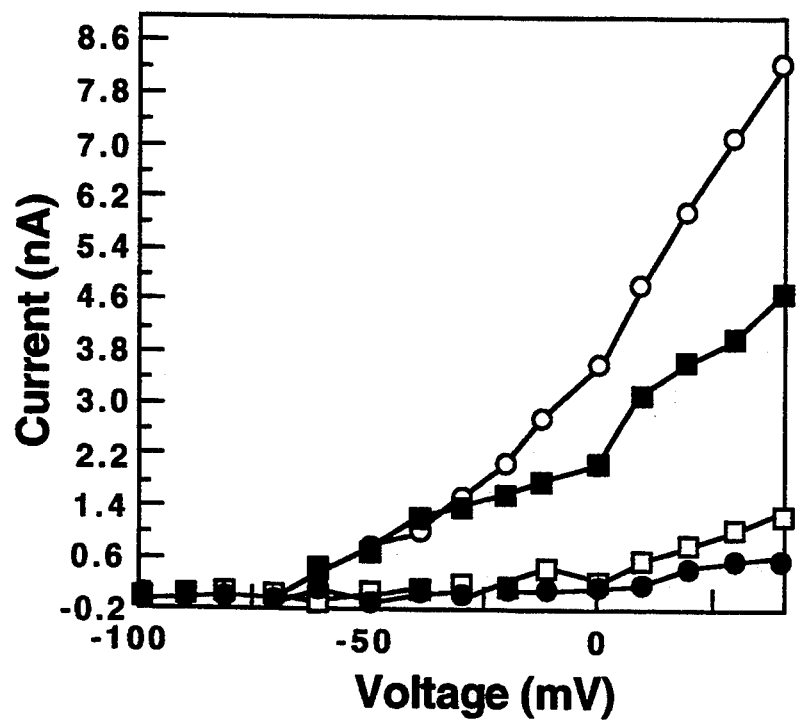
FIG. 15B illustrates the reversible inhibition of the radiation-induced currents (150 cGy) by 20 mM TEA (solid circles, non-irradiated cells; open squares, currents measured in the presence of 20 mM TEA following irradiation; solid squares, currents measured after removal of TEA; open circles, currents measured after irradiation but before the addition of TEA).

The experiments described in Example 14 provide data showing that the observed radiation-induced currents were indeed potassium currents. As illustrated in FIG. 15A, measured reversal potentials following 150 cGy $^{137}$Cs irradiation correlated well with $\ln([K+]_{ext}/[K+]_{int})$. In addition, as illustrated in FIG. 15B and detailed in Example 14, the radiation-induced currents could be inhibited by TEA, as expected for voltage-dependent potassium channel currents.

Figure 16A:
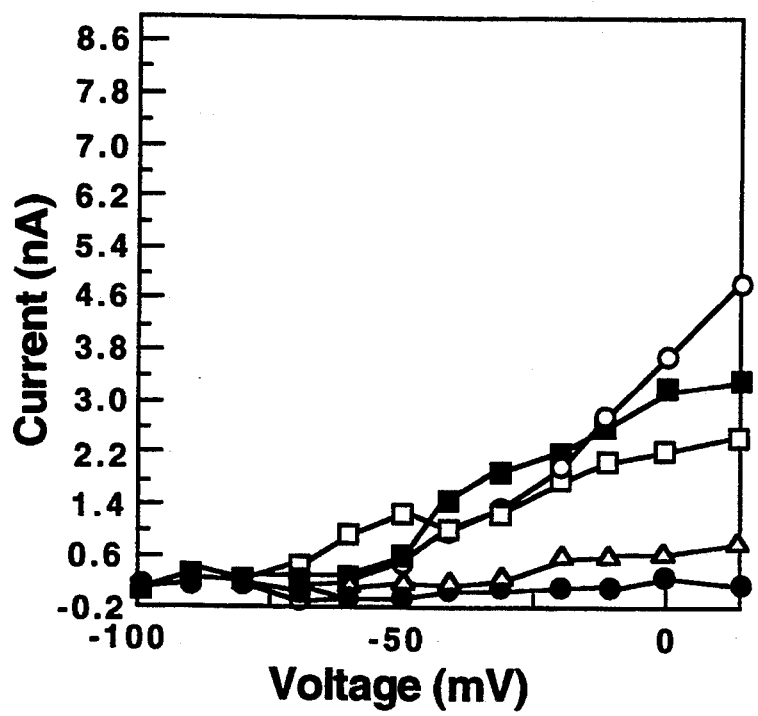
FIG. 16A shows voltage-dependent potassium currents measured at various times after irradiation (open circles, 5 min; solid rectangles, 30 min; open rectangles, 50 min; open triangles, 120 min; solid circles, control, non-irradiated cells).
Figure 16B:
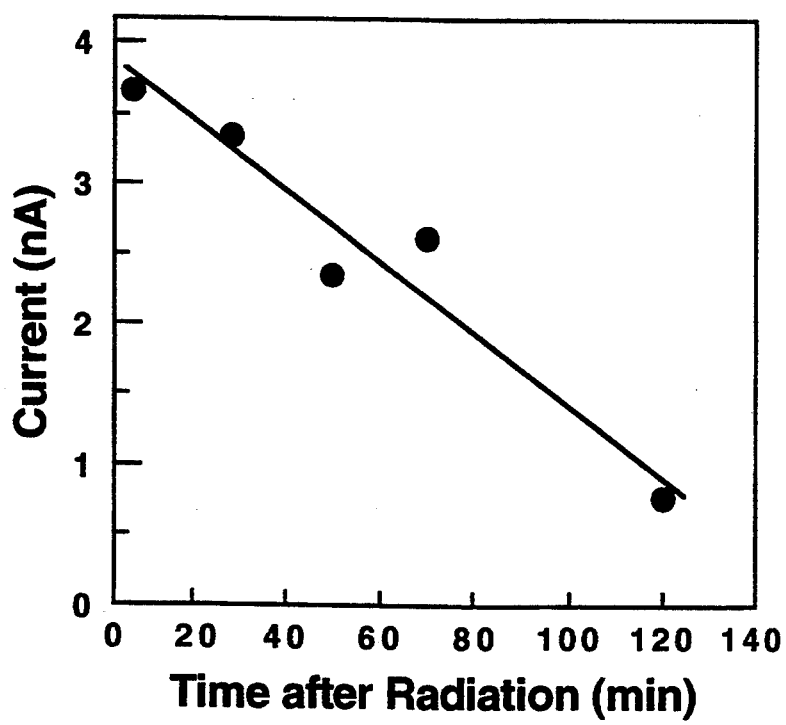
FIG. 16B shows a plot of the induced currents measured at 0 mV as a function of time after irradiation.

The appearance and decay of potassium currents induced in A549 cells by $^{137}$Cs irradiation (150 cGy) was monitored as detailed in Example 15. FIG. 16A shows the I-V relationships of currents measured at various times after irradiation (open circles, 5 min; solid rectangles, 30 min; open rectangles, 50 min; open triangles, 120 min; control, solid circles). FIG. 16B shows a plot of induced currents measured at 0 mV as a function of time after irradiation. As can be seen, the induced currents were maximal by the time the first current measurement was made (at ~5 minutes), and steadily decreased over the next two hours. The appearance of maximal current within the first 5 minutes showed that the induced current had not arisen from de novo channel protein synthesis.

Following the decay of the potassium current illustrated in FIG. 16B, the potassium channels remained refractory to induction by further gamma-irradiation for up to about 8 hours following the first irradiation. Small currents could be induced after about 12 hours, and a full response could be induced after about 15 hours.

Other experiments performed in support of the invention with a number of other cell lines have shown that protection from radiation generally correlates with heat-induced potassium currents.

In addition, in an experiment to examine whether DNA damage might be responsible for the induction of potassium current by the $^{137}$Cs-irradiation, A549 cells were incubated in medium containing 2 μCi/ml [$^3$H]thymidine for 16–18 hours prior to whole-cell recording (see Example 18). No potassium currents were observed, showing that K+ channels had not been activated by exposure to the [$^3$H]thymidine. This result suggests that DNA damage per se does not appear to induce voltage-dependent potassium currents.

C. Cellular Response to Other Cell-Damaging Stimuli

Although the invention is directed to assessing the response of a cell to cell-damaging energy, studies conducted in support of the invention suggest that potassium channel currents may be affected by a variety of other stimuli which may produce cellular damage. These include cell exposure to dimethylsulfoxide (DMSO), to free radical-producing chemical agents such as hydrogen peroxide, and to reoxygenation following exposure to hypoxic conditions (i.e., where the cells are deprived of oxygen).

Figure 7A:
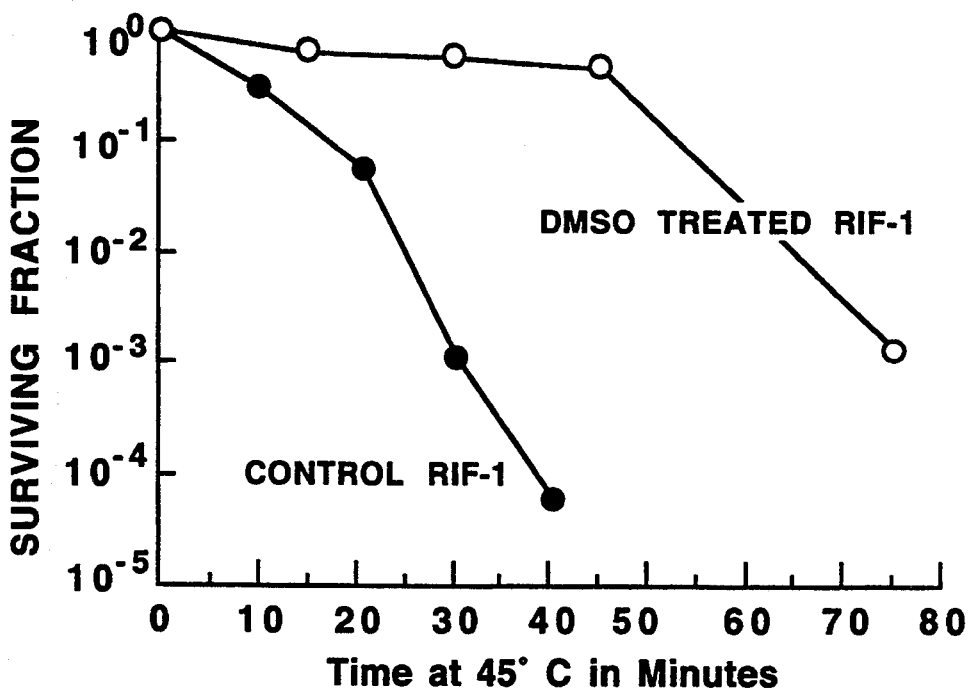
FIG. 7A shows the relative heat stabilities of RIF-1 cells grown for 7 days in the presence or absence of 2% (v/v) dimethylsulfoxide (DMSO). Following growth, the cells were heated for various durations and then assayed for survival by clonogenic assay.
Figure 7B:
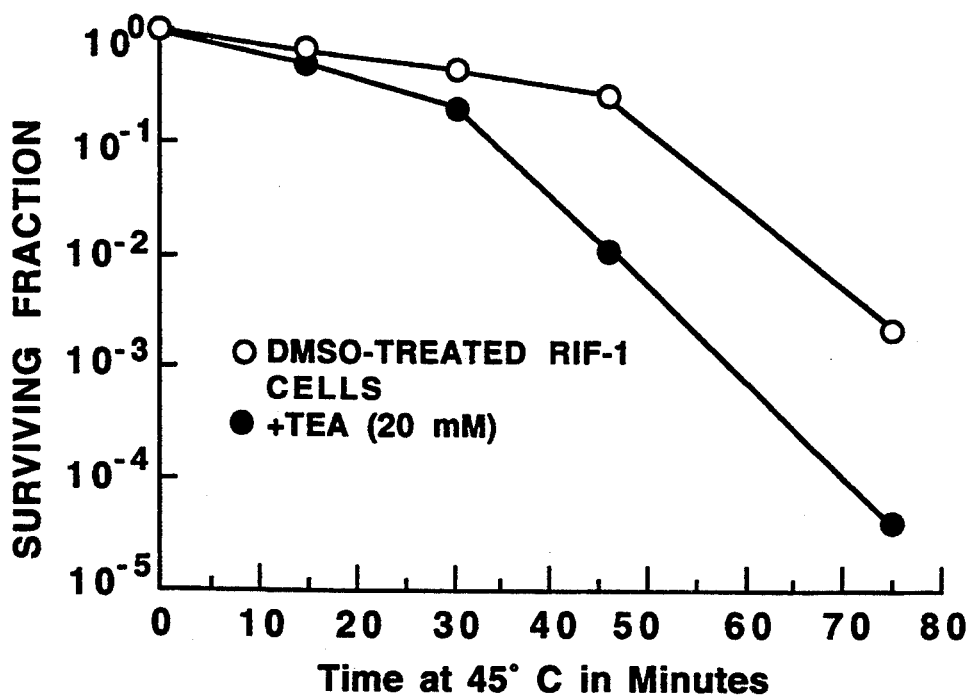
FIG. 7B shows the effect of TEA on the survival fraction of DMSO-treated cells.

Example 7 describes the induction of heat resistance in RIF-1 cells cultured in the presence of 2% (v:v) DMSO for seven days. Following the growth period, the sensitivity of the cells to various times of heating at 45° C. was assessed. As illustrated in FIG. 7A, RIF-1 cells cultured in 2% DMSO were significantly more heat resistant than cells that had not been so treated. In addition, the presence of 20 mM TEA in the medium during heating diminished heat resistance (FIG. 7B).

Figure 8:
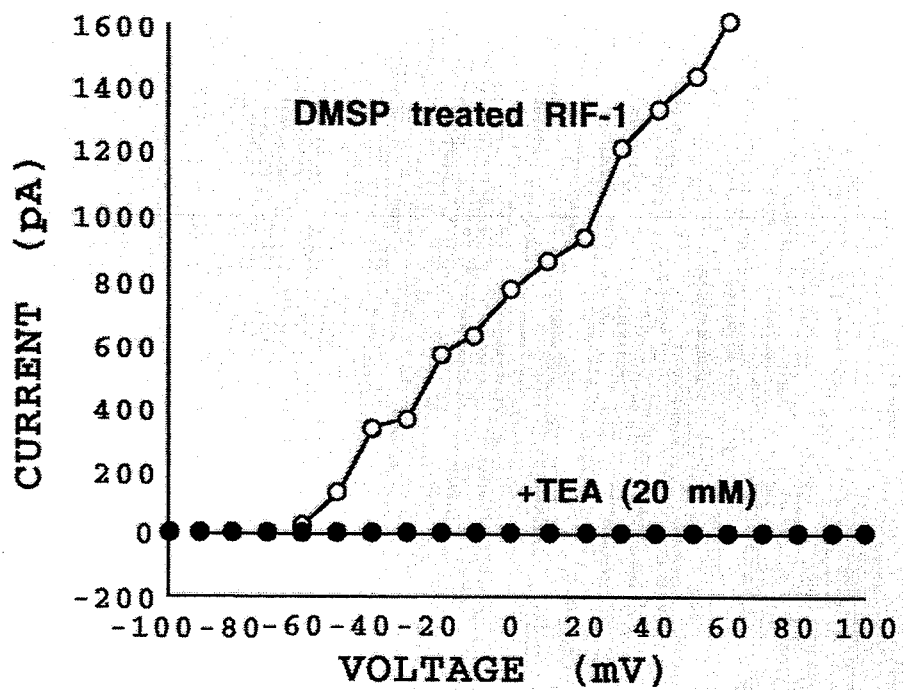
FIG. 8 shows heat-inducible voltage-dependent potassium currents measured in the presence or absence of 20 mM TEA for RIF-1 cells grown in the presence of 2% (v/v) DMSO. Prior to current measurements, the cells were heated at 45° C. for 10 min.

As described in Example 8, whole-cell voltage clamping experiments revealed that the DMSO-cultured cells of Example 7 exhibited voltage-dependent potassium currents following heating at 45° C. (FIG. 8). As also shown in FIG. 8, the presence of 20 mM TEA in the cell solution during current measurements virtually abolished the currents in the DMSO-cultured cells.

Figure 9:
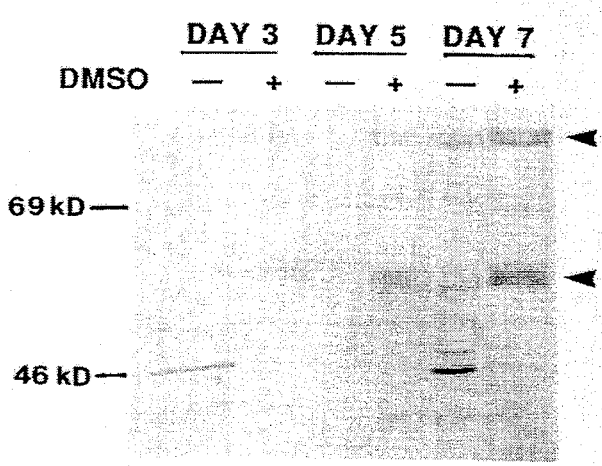
FIG. 9 shows a Western blot obtained with lysates of RIF-1 cells grown in the presence or absence of 2% (v/v) DMSO for 3, 5, and 7 days. Potassium channel proteins were detected using the ShA-3 antibody noted above for FIG. 5. Molecular weight markers (69 kD and 46 kD) are indicated on the left side of the Figure. Arrows indicate polypeptides expressed at an elevated level in the presence of DMSO.

The increased heat resistance noted above for the DMSO-treated RIF-1 cells correlated with increased synthesis of proteins recognized by the ShA-3 antibody. As noted above, the ShA-3 antibody is specific for ShakerB potassium channels (Schwarz et al., 1990). With reference to FIG. 9, which shows a Western blot of cell lysates resolved by SDS polyacrylamide gel electrophoresis, cells grown in the presence of 2% DMSO for 7 days contained two polypeptide doublets (marked by arrows in the figure) expressed at higher levels than in cells grown without DMSO. Further details of the experiment are described in Example 9.

The RIF-1 cells grown in the presence of 2% DMSO were also examined in terms of the effect of heat on levels of the heat shock protein hsp70. As detailed in Example 10, cells grown in the presence of 2% DMSO were briefly heat-treated (45° C., 10 minutes) and then analyzed by Western blot analysis directly after heat treatment, or after an additional 18 hour growth period. Cellular HSP70 levels were detected using antibodies that recognize both the constitutive (c) and heat-inducible (i) forms of hsp70. The results (FIG. 10) show that DMSO had no effect on the level of cellular HSP70, even after an 18 hour growth period to allow synthesis of inducible HSP70.

Figure 17:
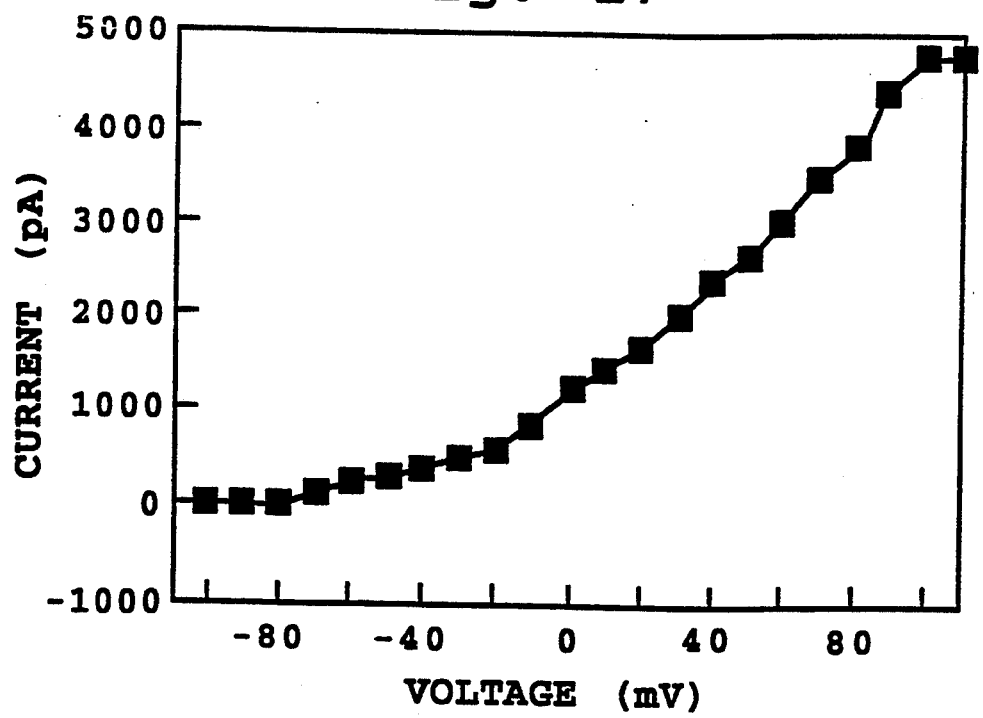
FIG. 17 illustrates a voltage-dependent potassium current observed in A549 cells following the addition of 3 μM hydrogen peroxide to the cell medium.

Further experiments carried out in support of the invention show that the free-radical producing compound hydrogen peroxide can also induce voltage-dependent potassium currents. As described in Example 17, A549 cells were whole-cell voltage-clamped, and the voltage-dependent potassium current was measured. Hydrogen peroxide was then added to the cell medium to a final concentration of 3.0 μM, and the current was measured again, giving rise to a sizeable voltage-dependent current (FIG. 17).

Figure 18:
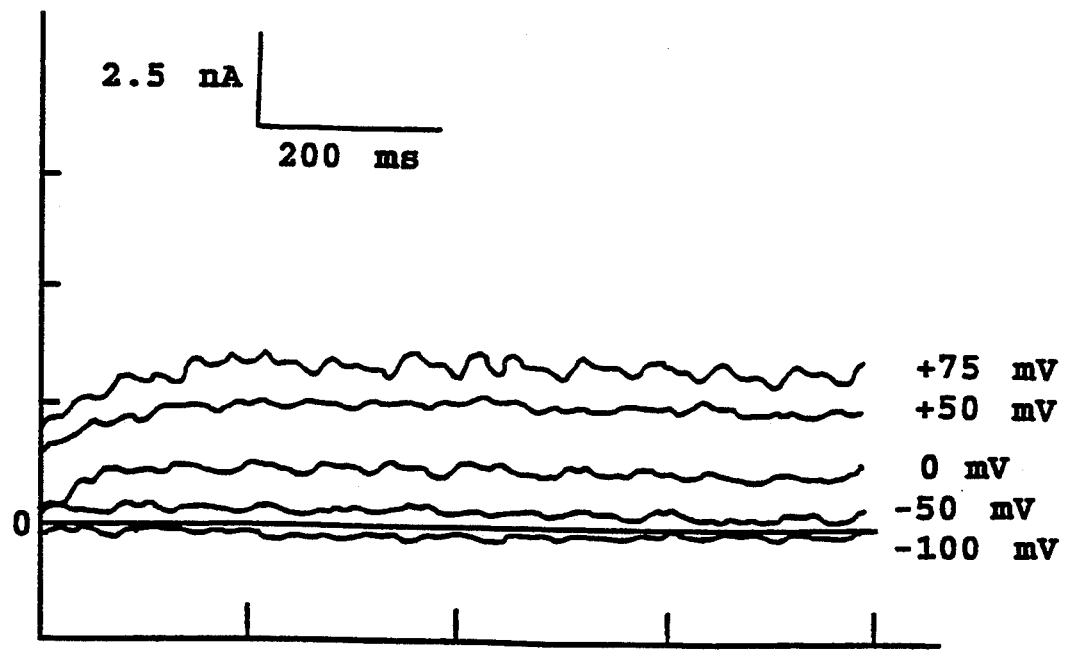
FIG. 18 shows a voltage-dependent potassium current observed in A549 cells following incubation under hypoxic conditions for 1 hour. The cells were re-exposed to air prior to currents measurements.

In another experiment, detailed in Example 19, A549 cells were incubated in an atmosphere of 5% $CO_2$/95% nitrogen for 1 hour to establish hypoxia in the cells, followed by exposure to air just prior to current measurements. As shown in FIG. 18, the hypoxic conditions produced voltage-dependent currents.

D. Applications

The methods described in this section can be used in optimizing treatment conditions for treating cancer cells in a human patient. In this general application, neoplastic cells obtained from the patient are examined, as above, for induction of potassium currents in response to ionizing radiation or elevated temperature. The level of response, in terms of induced potassium channel currents, can be used to guide the clinician in the selection of treatment modalities, exposure ranges, and treatment schedule.

X- or $\gamma$-irradiation is commonly used as a primary or adjunct therapy in the treatment of certain tumors. Exemplary neoplastic conditions include squamous cell carcinomas of the head and neck, and prostate carcinomas. The decision to treat a particular tumor or neoplastic condition with radiation therapy is based in part on the type of tumor and on its size and location.

In practicing this aspect of the invention, an isolated neoplastic cell is assessed for the presence of voltage-dependent potassium channels using any of the methods described in the sections above. In a preferred method, neoplastic cells are obtained from the patient prior to radiation treatment, and the cell is tested in vitro by electrophysiological methods essentially as described in the "Materials and Methods" section of the Examples, and in Examples 1 and 2. The presence and magnitude of a voltage-dependent potassium current are determined, and then the cells are exposed to a selected dose of cell-damaging radiation. The radiation exposure may be by irradiation with x- or $\gamma$-rays, or by high-energy gamma or beta emitters in contact with the cells, depending on the type of radiation treatment that is contemplated. Following exposure to the selected dose of cell-damaging radiation, the voltage-dependent potassium currents are again measured, to determine the increase in channel currents which has occurred in response to the radiation exposure.

Alternatively, the neoplastic cells may be exposed to a selected dose of radiation in vivo, and examined after such exposure in vitro for increases in potassium channel currents. This approach has the advantages of providing a more accurate gauge to a cell's response to treatment radiation, but has the disadvantage that the exposed neoplastic cells must be removed by biopsy and prepared for culture before current measurements may be made, precluding accurate current measurements immediately after the exposure to radiation.

The change in the measured current following exposure of the cell to the selected radiation dose provides a guide for the clinician in evaluating the dose of radiation which may be needed for effective treatment. A cell that shows little or no increase in channel currents can be expected to have greatest susceptibility to radiation, and therefore may be effectively treated at a relatively low radiation dose. Similarly, a sharp rise in channel currents, e.g. from 0-current before exposure to about 1,500–5,000 pA after exposure, indicates that the cell is likely to mount an effective resistance to radiation exposure, in which case higher total doses may be needed.

Since the cell will be expected to have defense mechanisms other than increased channel currents, and since the relative importance of these mechanisms may vary, it will be appreciated that the present method will provide one of perhaps several predictors of a cell's susceptibility to radiation treatment.

A similar approach may be employed to assess a cell's response to hyperthermia treatment. Briefly, a neoplastic cell obtained from the patient is grown in vitro or exposed in vivo to a heat source effective to elevate the cell temperature to, for example, 40°–45° C. for a selected heating period, e.g., 30–60 minutes. Before and after this exposure to heating, the cell's potassium channel currents are determined, as above, and the rise in current is used as a guide to the cell's susceptibility to heat treatment.

Studies conducted in support of the invention indicate that the radiation and heat treatment may operate independently in inducing channel currents. That is, a cell which has induced channel currents under a radiation stimulus may show a still further increase in channel currents when exposed to heat. This response may be exploited, for clinical purposes, to determine whether neoplastic cells from an individual may be susceptible to a treatment by both radiation and hyperthermia. For example, a cell which shows a strong response to radiation, but little or no further response to heat, may be best treated by first irradiating the cells, then treating with elevated temperature.

III. Drug-Screening Method

In another aspect, the invention includes a method for screening compounds which are effective to sensitize tumor cells to cell-damaging energy. The method includes incubating a test compound with a cultured cell that exhibits an inducible voltage-dependent potassium current upon exposure to cell-damaging energy.

Once the cells have reached a stable growth condition in the medium, a test compound to be screened is added to the culture medium, typically over a series of compound concentrations which are within the range of acceptable in vivo, e.g., blood concentrations, when the drug is administered to a human patient. In many cases, the concentration of a compound which can be tolerated in vivo will be known from literature data. Typically, the compound concentration in the culture medium will be between about. 10 nM to 100 $\mu$M.

After a selected period of compound uptake by the cell, e.g., 30–60 minutes, the cell is exposed to a cell-damaging energy treatment, as described in Section II above. Specifically, if the method is designed to identify compounds which may be effective in blocking cellular resistance to ionizing radiation, the cells are irradiated with x-rays or placed in contact with a high-energy emitter compound. One exemplary cell type for use in this application is A549 cell (ATCC #CCL185). A typical irradiation dose is between about 10 and 1500 cGy of $^{137}Cs$ $\gamma$-radiation.

After a selected period of exposure, the cells are again examined for channel currents, e.g., by whole cell voltage-clamping. The change in channel currents, in the presence and absence of the test compound, is used as an indicator of the test compound's ability to block induction of increased potassium currents in response to the radiation exposure.

Example 16 suggests one general type of compound which may be screened in this assay. In this study, a thiol was added to the cell culture during current-induction by radiation. The presence of the thiol (N-acetylcysteine) was effective to substantially reduce current induction, possibly by limiting free radical concentration in the irradiated cells. A variety of other compounds, such as $\alpha$-tocopherol, desferol, and ascorbic acid which are known to protect cells against free radical damage are likely candidates for screening by the method.

A similar approach may be employed in screening compounds which are effective to sensitize tumor cells to damage by hyperthermia. Here the cells are exposed to heat treatment in the presence and absence of the test compound. The change in channel currents, in the presence and absence of the test compound, is then used as an indicator of the test compound's ability to block induction of increased potassium currents in response to the heat.

In one exemplary method, the cell is exposed to a temperature of about 45 degrees C., for a period of between about i and 45 minutes.

IV. Transfected Cells with Elevated Potassium Currents

A. Isolation of VDPC protein

In accordance with the present invention, it has been discovered that cells that are particularly insensitive to radiation contain high constitutive levels of stress-induced potassium channels (VDPC) of the radiation inducible form. Likewise, heat resistant cells, such as TR-4 cells, express high levels of VDPC of the heat inducible form, as evidenced by electrophysiological studies described above and by enhanced immunoreactivity with ShA-3 anti-potassium channel antibodies, as shown in FIG. 5. Heat inducible VDPCs appear in TR-4 cells as protein bands migrating at about 61 kD, 66 kD, and 74 kD.

VDPC can be conveniently isolated from cell lines or tumors having high constitutive levels of the channel proteins, such as from TR-4 cells. In methods contemplated by the present invention, such cells are isolated and the membranes extracted using one or more detergents known in the art to preserve biological function. Typically, non-ionic detergents are used. Solubilized membrane extracts are tested for the presence of VDPC, by immunoreactivity with polyclonal antibody ShA-3, or an equivalent VDPC-reactive antibody. Such immunoreactivity is conveniently observed in a gel Western blot assay, as described in the Examples section under "Materials and Methods" below. Solubilized detergent-containing extracts are then fractionated by one or more chromatographic methods known in the art. According to established procedures for detergent solubilized proteins, suitable chromatographic methods depend on the type and concentration of detergent present in the extract and include but are not limited to size exclusion gel chromatography and hydrophobic chromatography, carried out by conventional column chromatographic methods, including high performance liquid column (HPLC) chromatography. Chromatographic fractions are tested for the presence of VDPC by immunoreactivity as above. An immunoaffinity purification step, utilizing immobilized ShA-3 antibodies or equivalent antibodies is used to achieve further purification.

The above described procedures are contemplated to yield a substantially purified VDPC protein. This protein can be used in screening of compounds that bind the channel protein and in generation of specific anti-VDPC antibodies.

B. Isolation of VDPC Coding Sequence

VDPC coding sequences are preferably isolated from cells expressing high constitutive levels of the channel protein, as described above. Generally, strategies and methods for isolating gene coding sequences are now considered standard in the art. However, the success of any one method for isolating a coding sequence for a particular protein is dependent on the possession of certain tools or reagents, such as have been identified in accordance with the present invention.

In one preferred method of isolating a gene coding sequence for an VDPC protein, potassium channel-specific oligonucleotide primers are made according to standard methods (see Example 20). For use in the invention, suitable oligonucleotide primers include forward oligonucleotide primer SEQ ID NO: 1 and reverse oligonucleotide primer SEQ ID NO: 2, shown in FIG. 20. These primers are based on the highly conserved S4-S6 transmembrane domain regions of HBK2, a human voltage-gated K+ channel gene. The primers are used to amplify genomic DNA coding regions derived from VDPC containing cells, such as A549 cells. Such coding regions are isolated and used to construct oligonucleotide probes for screening cDNA libraries, such as AB1522 and A549 cDNA libraries.

Bacterial clones or phage plaques which hybridize to the oligonucleotide probes on duplicate filters are isolated by PCR using vector-based oligonucleotide sequences to amplify the inserts contained in these clones. Restriction mapping can be used to characterize the clones and to eliminate redundancy in the number of K+ channel sequences analyzed. Such K+ channel sequences are then radiolabeled and hybridized to Northern blots containing mRNA derived from a series of normal and transformed cell lines which show increased K+ currents after exposure to ionizing radiation or heat. Hybridizing mRNA is then sequenced and compared to known voltage-gated potassium channel sequences.

Alternative methods of cloning the VDPC gene are also contemplated by the present invention. cDNA libraries are prepared from VDPC containing cells in the expression vector lambda gt11. cDNA sequences are then selected for expression of peptides which are immunoreactive with an VDPC-recognizing antibody, such as ShA-3, described above. The nucleic acid coding sequences identified by this approach serve as useful hybridization probes for the identification of further VDPC coding regions, from further bacterial cDNA libraries, such as a lambda gt10 library and/or genomic libraries. Full length VDPC coding genes can be obtained directly or by ligating that portion of the genomic clone missing from the K+ channel to make a full length "hybrid gene." Alternatively, full length genes can be made from the genomic clone by PCR.

Verification of the identity of the isolated gene is made by one or more of several assays. Each K+ channel clone is expressed in mammalian cells using mammalian expression vectors with strong promotors such as the CMV promotor. The presence of a functional VDPC is then verified by electrophysiological methods, as described in part II above. Alternatively in vitro transcribed RNA is microinjected into frog oocytes, and the potassium currents in the cells are compared to VDPC currents.

C. Transfection of Cells

Cells containing elevated levels of VDPC can be used in a number of applications, in accordance with the invention. One use of such cells is in the screening method of the invention. In this application, it would be useful to have a relatively uniform population of cells expressing high constitutive levels of VDPC. Such a population can be produced by stably transfecting a cell line, such as RIF-1 cells or A549 cells with a plasmid containing the VDPC gene isolated as described above. Cells are transfected according to one or more methods known in the art. A preferred method is electropotation. VDPC content of transfected cells is quantitated by reactivity with VDPC-reactive antibodies and/or by electrophysiological techniques, as described above.

Heat inducible VDPC-containing cells also find use, in accordance with the present invention, in providing cells for use in production of certain biological products, such as peptide hormones. In this embodiment of the invention, producer cells are transfected with the VDPC, as described above. Such genetically engineered cells are anticipated to have the temperature resistance characteristics of the TR-4 cell described herein, while retaining their ability to make the product of interest. By having the capability to grow at an elevated temperature, such cells are anticipated to exhibit increased cellular enzymatic production of the product.

The following examples illustrate, but are not in any way intended to limit the scope of the invention.

EXAMPLES

Materials and Methods

Chemicals. Tetraethylammonium chloride (TEA), $H_2O_2$, and N-acetylcysteine were purchased from Sigma.

Cell Lines and Culture Conditions. RIF-1 and TR-4 cells (Hahn and van Kersen, 1988; Anderson et al., 1989) were grown in exponential phase in RPMI-1640 with 10% FBS (fetal bovine serum) or 10% FCS (fetal calf serum), 200 μg/ml streptomycin, and 200 units/ml penicillin G.

A549 cells were obtained from the American Type Culture Collection (ATCC#CCL185) and were routinely cultured in α-MEM containing 10% FCS, 100 μg/ml streptomycin, and 200 units/ml penicillin. All cells were incubated in 5% $CO_2$ at 37° C. unless noted otherwise.

Voltage-Clamp Recordings. Whole-cell recording was performed by voltage clamp analysis as described by Hamill et al. (1981). In general, prior to whole cell recording, the cell medium was replaced with serum-free medium to ensure a better giga-ohm seal. Glass electrodes were prepared using a vertical pipette puller (model P30 from Sutter Instruments, Calif.). The tip diameter to be achieve depended upon the size of the cell-type being examined, but was generally between about 0.5 and 1 μm. Glass electrodes having a tip resistance of 3–7 Mohms were sylgarded (with Sylgard, Dow Chemical) and backfilled with a solution containing 140 mM KCl, 2 mM $MgCl_2$, 11 mM EGTA, 1 mM $CaCl_2$, and 10 mM Hepes, pH 7.2. A Narashige XYZ micromanipulator was used to position the tip of the microelectrode over a cell. A test pulse of 20 mV was applied, and the cell was then aspirated against the tip of the microelectrode. The membrane seal resistance was determined from the reduction in voltage of the test pulse.

Membrane currents were filtered at 2 kHz using a 4-pole low pass Bessel filter before sampling with a 12-bit digital-analog converter controlled by a Labmaster board (Scientific Solutions) in an IBM AT computer. Leakage currents were subtracted from the total currents measured at each voltage either by using a p,p/4 algorithm (Armstrong and Bezanilla, 1974) built into the software (INDEC Systems, Santa Cruz, Calif.), or after determining the linear component from the current-voltage (I-V) relation near the holding potential of −75 mV. The limit of sensitivity of the current measurements in these experiments was about 50–60 pA.

In general, cells were whole-cell voltage-clamped immediately after the heating and irradiation treatments described in the examples below.

γ-irradiation. Cells were irradiated at room temperature using a $^{137}$[Cs] source at a dose rate of 150 cGy/min. The $^{137}$[Cs] source consisted of a Mark I irradiator (model 30, 2000 Ci $^{137}$[Cs]) from J. L. Shepherd and Associates (Glendale, Calif.). Unless noted otherwise, the cells were incubated at 37° C. after irradiation for further characterization.

Western Blot Analysis In general, following separation of cellular proteins by sodium dodecyl sulfate (SDS)-polyacrylamide gel electrophoresis, separated proteins were electroblotted onto a nitrocellulose membrane using a 25 mM Tris-HCl/192 mM glycine/20% (v/v) methanol transfer buffer (pH 8.3) in a Trans-Blot apparatus (Bio-Rad, Richmond, Calif.) at 15 V and 100 mA for 12 to 14 h. The blot was blocked in 5% nonfat dry milk in TBS (50 mM Tris containing 0.2 M NaCl, pH 7.4) at room temperature for 1h; this step and all following steps were done with continuous agitation. The primary antibody was diluted 1:200 in 3% nonfat dry milk in TBS, and the blot was incubated for 16 to 24 h at 4° C. The blot was washed with TBS three times for 10 min per wash, and incubated for 2 h at room temperature with a 1:500 dilution of alkaline phosphatase-conjugated antispecies antibody. After washing with TBS as above, the blot was developed by incubation for 20 min in a solution containing 3-hydroxy-2-naphthoic acid 2,4-dimethylanilide phosphate (1 μg/ml) and fast red (2 μg/ml) in TBS buffer. The developed blot was washed in distilled, deionized water to stop the color reaction.

EXAMPLE 1

Heat-Induced Activation of K+ Channel Currents in TR-4 Cells

RIF-1 and TR-4 cells were grown in sterile 60 mm NUNC dishes (Intermed, Denmark) and incubated overnight in RPMI-1640 medium (GIBCO, Grand Island, N.Y.) supplemented with 10% fetal bovine serum (FBS). Prior to current measurements, the cells were heated at 45° C. for 10 minutes, and then returned to 37° C. Potassium currents were then measured using 100 millisecond voltage steps to −100, 50, 0, and 50 mV, which were delivered from a 500 millisecond prepulse of −120 mV. The holding potential was −75 mV.

Time courses of currents measured with TR-4 cells are shown in FIG. 1A, with corresponding data for RIF-1 cells shown in FIG. 1B for comparison. Note that the currents measured with the RIF-1 cells was virtually indistinguishable from background. In addition, no currents were detected for unheated RIF-1 and TR-4 cells.

EXAMPLE 2

Effect of Tetraethylammonium Ions on Heat-Induced K+ Channel Currents

TR-4 cells were treated as in Example 1, except that after the heat treatment, voltage dependent currents were measured before and after the addition of tetraethylammonium chloride (TEA, 20 mM final concentration) to the cell medium. The results are shown in FIG. 2, where open circles represent current measured in the absence of TEA, and closed circles represent current measured in the presence of 20 mM TEA.

EXAMPLE 3

Dependence of Reversal Potential on K+ Concentration

TR-4 cells were heated at 45° C. for 30 minutes in RPMI-1640 supplemented with 10% FBS. The medium was replaced with solutions containing the same high K+ solution used to fill the glass electrode. A 100 millisecond voltage step to +50 mV from a holding voltage of −75 mV was followed by a 50 millisecond postpulse at 50 mV, during which tail currents were recorded. In subsequent cycles, the postpulse voltage was decreased in steps of 10 mV to determine the reversal potential. The reversal potential was determined similarly at lower external concentrations of K+ as well. The results are shown in FIG. 3.

EXAMPLE 4

Effect of TEA on Cell Survival After Heating

RIF-1 and TR-4 cells were grown as described in Example 1. To measure the effect of TEA on cell survival following heating, dishes containing the cells were heated at 45° C. for various lengths of time (in the range of 0–100 min) with or without TEA (20 mM final concentration) added to the cell medium. The cells were trypsinized and plated using appropriate dilutions for colony formation. As can be seen from FIG. 4, the TR-4 cells were made sensitive to heat in the presence of TEA, but TEA showed no effect on the survival rate of the RIF-1 cells.

EXAMPLE 5

Expression of K+ Channel Proteins in TR-4 Cells

RIF-1 and TR-4 cells were grown in exponential phase at 37° C. in RPMI-1640 medium supplemented with 10% FBS. Cellular proteins were separated by sodium dodecyl sulfate (SDS)-7.5% polyacrylamide gel electrophoresis using the method of Laemmli (Nature 227:680–685). Each sample lane contained 30 μg of protein. Western blot analysis (see Materials and Methods) was performed using ShA-3, a polyclonal rabbit antibody that recognizes ShakerB K+ channel proteins (Schwarz et al., 1990). The results are shown in FIG. 5 (lane 1: molecular weight markers; lane 2: RIF-1 cell lysate; lane 3: TR-4 cell lysate).

EXAMPLE 6

Blockage of Heat-Induced HSF Activation in TR-4 cells by TEA

To determine whether the presence of TEA during heating prevented the activation of heat shock factor (HSF), RIF-1 and TR-4 cells grown as in Example 1 were heated at 45° C. for 15–40 minutes in the presence or absence of 20 mM TEA in the medium. After being washed with fresh medium (no TEA), the cells were harvested, and gel retardation assays were performed as described by Zimarino et al. (1987), except that the electrophoresis was performed on a 4.5% native polyacrylamide gel in 0.5X TBE buffer (45 mM Tris-borate, 1 mM EDTA) at 140 V at room temperature for 2.5 h. The gel was fixed by soaking in 7% acetic acid for 5 min, rinsed briefly in distilled water, and dried on Whatman 3 MM chromatography paper. The gel was then autoradiographed by exposing Kodak XAR-2 film to the gels at −70° C. with intensifying screens (Cronex Lighting Plus, Dupont).

The results are shown in FIG. 6, wherein the time of heating at 45° C. and the presence or absence of 20 mM TEA is indicated above each lane; the absence or presence of cold competitor HSE oligonucleotide is denoted by "−" or "+", respectively.

EXAMPLE 7

Induction of Heat Resistance in RIF-1 Cells Treated with DMSO

RIF-1 cells were grown at 37° C. in RPMI-1640 medium supplemented with 10% FBS and 2% (v/v) DMSO (dimethylsulfoxide). After seven days of growth, the medium was replaced with DMSO-free medium, and the heat sensitivity of the cells in the presence and absence of 20 mM TEA was determined by clonogenic assay as in Example 4. The results are shown in FIGS. 7A and 7B, with survival data for non-DMSO-treated RIF-1 cells shown for comparison.

EXAMPLE 8

Potassium Currents of DMSO-Treated RIF-1 Cells

The potassium currents of RIF-1 cells grown in the presence of 2% DMSO as above (Example 7) were determined in the presence and absence of 20 mM TEA following heating of the cells at 45° C. for 10 minutes, as in Example 2. The results are shown in FIG. 8.

EXAMPLE 9

Increased Expression of K+ Channel Protein in RIF-1 Cells Exposed to DMSO

RIF-1 cells were grown in RPMI-1640 containing 10% FBS and 2% DMSO for up to 7 days, followed by SDS polyacrylamide gel electrophoresis and Western blot analysis using antibody ShA-3 as in Example 5. The results after 3, 5, and 7 days of growth in the presence of 2% DMSO are shown in FIG. 9. The figure shows that the abundance of K+ channel proteins recognized by antibody ShA-3 increased with increasing duration of exposure of the cells to DMSO (+ headings), in comparison to the levels observed with cells that had not been treated with DMSO (−headings).

EXAMPLE 10

HSP70 Levels in RIF-1 Cells Are Not Affected by DMSO Treatment

RIF-1 cells were grown for 7 days in the presence of 2% DMSO as in Example 9. After the seventh day, cells were heated at 45° C. for 10 min, and were analyzed either immediately by SDS gel/Western blot analysis, or after an additional 18 hour growth period at 37° C. to allow synthesis of heat-inducible HSP70 polypeptides. Western blot analysis entailed the use of N-27, a monoclonal mouse antibody that recognizes both constitutive and inducible HSP70 polypeptides (Riabowl et al., 1988). Cells that were not heated were included as a control. The results are shown in FIG. 10. Note that the arrows on the right side of the figure show the positions of the constitutive (c) and inducible (i) forms of HSP70.

EXAMPLE 11

Effect of TEA on RIF-1 Cells Transfected with the ShakerB Gene

RIF-1 cells were transfected with a plasmid containing the ShakerB gene (pGWI-CMV, supplied by British Biotechnology Ltd., Oxford, U.K.) by electropotation using a Cell Porator (Bio-Rad, Richmond, Calif.) at 150 V and 1180 $\mu$F in Hanks' buffered saline solution. Cells were also mock-transfected under identical conditions, but in the absence of the plasmid. Following transfection, the cells were incubated at 37° C. for 14 h, and following a change to fresh RPMI-1640 medium containing 10% FBS, the cells were incubated for another 2 days to allow expression of the transfected gene prior to heat and TEA experiments. The cells were heated at 45° C. for various times ($\sim$0–100 min) and then plated to determine survival fraction. The results are shown in FIG. 11.

In a parallel set of experiments, heating of the mock- and gene-transfected cells was performed in the presence or absence of 20 mM TEA, and the expression of HSP70 proteins was determined by immunoblot analysis, using the HSP70-specific N-27 antibody as in Example 10. As seen from FIG. 12, the inhibitory effect of TEA on expression of HSP70 (both the constitutive (c) and inducible (i) forms) was greater in the cells transfected with the ShakerB gene than in mock transfected cells.

EXAMPLE 12

Absence of an Effect Of TEA on the Development of Thermotolerance in TR-4 Cells

The development of thermotolerance in TR-4 cells in the presence or absence of 20 mM TEA was assessed by heating the cells at 45° C. for 40 min, followed by a 12 h incubation at 37° C. (Hahn and van Kersen, 1988), and assessment of cell survival following heating and clonogenic assay as described in Example 4. Five groups of TR-4 cells (a to e) were examined, differing only as to which steps of the procedure included TEA in the cell medium. The five groups were (a) a TEA-free group that was not exposed to TEA, (b) a group exposed to TEA only during the 40 min heating period, (c) a group exposed to TEA only during the 12 h incubation, (d) a group exposed to TEA during heating and the subsequent incubation period, and (e), a control group that had not been heated and therefore had not been rendered thermotolerant.

The results are shown in FIG. 13 (open squares, control group (e); solid squares, TEA-free group (a); solid circles, TEA group (d). Since the data for groups b-d were very similar, data for only group d are shown for clarity.

EXAMPLE 13

Dose Dependence of Radiation-Induced K+ Channel Currents

In this study, voltage-dependent K+ currents were determined by whole-cell voltage-clamping of A549 cells that had been exposed to 0 (control), 10, or 150 cGy $\gamma$-radiation from the $^{137}$Cs source described in the Materials and Methods section. The radiation-induced currents, measured within 20 minutes of irradiation, are shown in FIG. 14A: solid circles, no irradiation; open squares, 10 cGy; open circles, 150 cGy. As can be seen from FIG. 14A, irradiation with 10 cGy produced K+ currents that were readily distinguishable from the background provided by the control cells. Substantially higher currents were induced with a 150 cGy exposure.

FIG. 14B shows a plot of radiation-induced currents (measured at 0 mV) versus radiation dose.

In another experiment, cell survival of A549 cells was measured as a function of $^{137}$Cs irradiation dosages (0–1000 cGy) in the presence or absence of 20 mM TEA in the cell medium during irradiation. The results are show in FIG. 14C.

EXAMPLE 14

Assignment of Radiation-Induced Currents in A549 Cells to K+ channels

The origin of the radiation-induced currents was determined on the basis of two studies.

In one study, following irradiation with 150 cGy, the dependence of reversal potential of the induced currents on extracellular K+ concentration was determined by the approach described in Example 3. As shown in FIG. 15A, the observed reversal potential (solid circles) correlated well with those expected from the Nernst equation (open circles).

In a second study, to determine whether the induced currents -were affected by the presence of TEA, A549 cells were exposed to 150 cGy of 137Cs $\gamma$-irradiation, and the radiation-induced currents were measured under three different conditions: (a) directly after irradiation, (b) after replacement of the bath solution with medium containing 20 mM TEA and (c) after the TEA solution of step (b) had been replaced with TEA-free medium.

The results are shown in FIG. 15B (solid circles, non-irradiated cells; open squares, currents measured in the presence of 20 mM TEA following irradiation; solid squares, currents measured after removal of TEA; open circles, currents measured after irradiation but before the addition of TEA).

EXAMPLE 15

Time Course of K+ Current Levels in A549 Cells Following 150 cGy Irradiation

In this study, A549 cells were irradiated with 150 cGy ($^{137}$Cs), and the appearance and decay of the induced K+ currents was monitored by whole-cell recording at 37° C. The voltage-dependent currents at various times after irradiation are shown in FIG. 16A and 16B. FIG. 16A shows the I-V relationships of currents measured at various times after irradiation (open circles, 5 min; solid rectangles, 30 min; open rectangles, 50 min; open triangles, 120 min; control, solid circles). FIG. 16B shows a plot of the induced currents measured at 0 mV as a function of time after irradiation.

EXAMPLE 16

Effect Of N-Acetylcysteine on the Induction of K+ Currents by Irradiation

Figure 19:
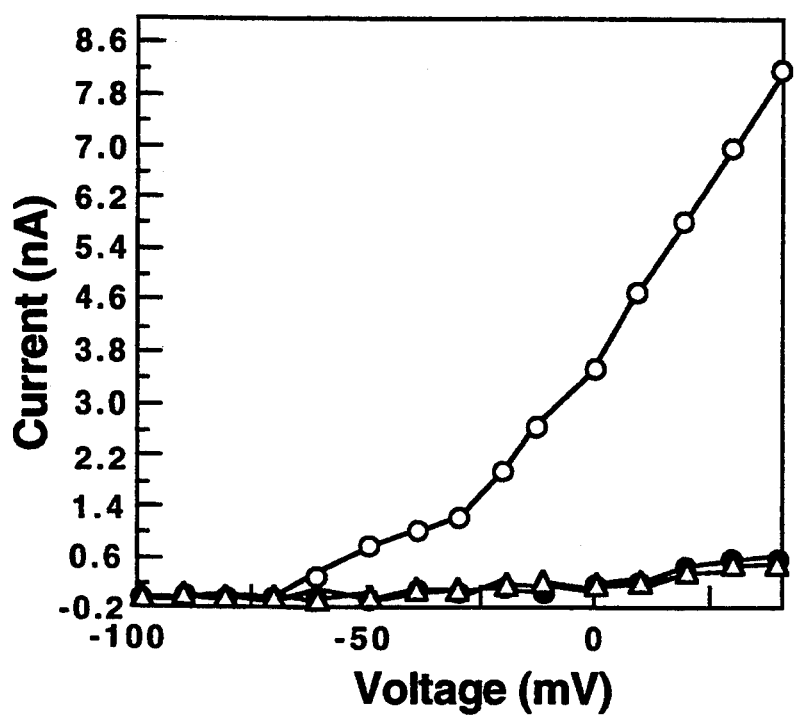
FIG. 19 shows the effect of 20 mM N-acetylcysteine on the induction of potassium currents in A549 cells by irradiation. Cells were preincubated for 1 h in medium containing 20 mM N-acetylcysteine (NAC). While still in the presence of NAC, the cells were irradiated (150 cGy), and the induced currents were recorded (open circles, irradiation without NAC preincubation; open triangles, irradiation following preincubation with 20 mM NAC; solid circles, non-irradiated control cells).

A549 cells grown as described in the Materials and Methods section were preincubated for 1 h in medium containing 20 mM N-acetylcysteine (NAC) (Schreck et al., 1991). The cells, still in the presence of NAC, were then irradiated (150 cGy), and the induced currents were recorded. The results are shown in FIG. 19 (open circles, irradiation without NAC preincubation; open triangles, preincubation with 20 mM NAC; solid circles, non-irradiated control cells).

EXAMPLE 17

Induction of K+ Currents with Hydrogen Peroxide

Following whole-cell voltage-clamping of A549 cells, the background level of potassium current was measured, and hydrogen peroxide was then added to the cell medium to a final concentration of 3.0 μM. Within 30 seconds of addition of hydrogen peroxide, the current was measured again. The results are shown in FIG. 17.

EXAMPLE 18

[³H]Thymidine Treatment of Cells

To examine whether DNA damage is responsible for K+ current induction, cells were incubated in e-MEM containing 2 μCi/ml [³H]thymidine (20 Ci/mmol (Amersham) for 16–18 hours prior to whole-cell recording. No potassium currents were observed.

EXAMPLE 19

Induction of Potassium Currents by Hypoxia

A549 cells were plated on glass coverslips which were placed in sterile 60 mm glass petri dishes containing 5 ml of e-MEM (minimal essential medium). Following overnight incubation at 37° C. in an atmosphere of 5% $CO_2$/95% air, the medium was replaced with fresh medium, and the petri dishes were placed in individual aluminum containers designed for gas exchange. The atmosphere in the chambers was reduced in pressure to less than 1 psi, and then replenished with a mixture of 5% $CO_2$- 95% nitrogen while being agitated on a reciprocating shaker. The evacuation and replenishment steps were repeated at least twice more to further remove oxygen (5 gas exchange cycles took less than 15 minutes). After the gas exchange steps, the aluminum chambers were sealed and incubated for 37° C. on a reciprocating shaker for 1 hour. The seals were then broken, and potassium channel currents were measured as in Example 1. The results are shown in FIG. 18.

EXAMPLE 20

Isolation of VDPC Specific Oligonucleotide Probes

Oligonucleotide primers shown in FIG. 20 were prepared in an automated oligonucleotide synthesizer, according to standard methods. These probes were directed to the highly conserved S4-S6 transmembrane domains of a human brain voltage-gated potassium channel gene (HBK2; Grupe et al., 1990) and were used to amplify cDNA and genomic DNA coding regions from normal fibroblasts by polymerase chain reaction (PCR) according to standard methods (Ausubel et al., 1992). Magnesium chloride and nucleotide concentrations were adjusted to eliminate amplification of false DNA fragments. A 225 bp DNA fragment was obtained and cloned into the vector pCRII (Invitrogen, San Diego, Calif.). Following transfection of the vector, ten clones were selected, grown, and subjected to restriction digestion to verify the proper size inserts. Four of these clones were sequenced using the Sanger dideoxy chain termination technique (Sanger). A partial sequence of one clone, designated AG8 (SEQ ID NO: 3; FIG. 21) was found to match the sequence of the human voltage-gated potassium channel K1 (SEQ ID NO: 4; FIG. 21). Three of the clones were identical to the S4 to S6 region of HBK2 (Grupe et al., 1990).

Although the invention has been described with respect to particular embodiments, it will be appreciated that various changes and modifications can be made without departing from the invention.

---

It is claimed:

1. A method of assessing the susceptibility of a cell of a known origin to cell-damaging energy, comprising
    exposing a cell from a known origin to an amount of cell-damaging energy effective to increase a potassium channel current in said cell,
    measuring a voltage-dependent potassium current in a cell from the known origin, before and after said exposing, and
    using the change in the measured current before and after exposing, to assess the ability of a cell from the known origin to resist said energy.

2. The method of claim 1, wherein said cell-damaging energy is ionizing radiation.

3. The method of claim 2, wherein said cell damaging energy is x-irradiation.

4. The method of claim 2, wherein said exposing includes contacting the cells with a high-energy radiation emitter.

5. The method of claim 1, wherein said cell-damaging energy is heat.

6. The method of claim 5, wherein said heating is carried out by microwave irradiation.

7. The method of claim 5, wherein said heating is carried out by elevating the temperature of the cell, in vitro.

8. The method of claim 1, for use in optimizing treatment conditions for treating cancer cells in a human patient, wherein the origin of the cell being assessed is a population of cancer cells from the patient's body, and said measuring step is carried out on said cell in vitro.

9. The method of claim 8, wherein said exposing and measuring steps are carried out on the cell of known origin cultured in vitro.

10. The method of claim 8, wherein said exposing includes exposing a portion of the patient, and said measuring includes measuring the potassium currents of cells obtained from the exposed portion of the body before and after said exposing.

11. A method for screening compounds which are effective to sensitize tumor cells to cell-damaging energy, comprising incubating a test compound with a cultured cell that exhibits an inducible voltage-dependent potassium current upon exposure to cell-damaging energy, during said incubating, exposing the cell to an amount of the cell-damaging energy effective to increase a potassium channel current in said cell, measuring the voltage-dependent potassium current in the cell before and after said incubating, and using the change in voltage-dependent potassium current measured before and after said incubating as an indicator of the test compound's ability to block induction of increased potassium currents in response to exposure to cell-damaging energy.

12. The method of claim 11, wherein the potassium current is measured by whole cell voltage-clamping.

13. The method of claim 11, wherein said cell-damaging energy is ionizing radiation.

14. The method of claim 13, wherein the cell is exposed to between 10 and 1500 cGy of $^{137}$Cs $\gamma$-radiation.

15. The method of claim 13, wherein the cell is an A549 cell.

16. The method of claim 11, wherein said cell-damaging energy is heat.

17. The method of claim 16, wherein the cell is exposed to a temperature of about 45 degrees C, for a period of between 1 and 45 minutes.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: FORWARD OLIGONUCLEOTIDE PRIMER, FIG.20

( x i ) SEQUENCE DESCRIPTION: SEQ ID NO:1:

CAGGCCTCCA TGAGGGAGCT GGGG        24

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
    ( C ) INDIVIDUAL ISOLATE: REVERSE OLIGONUCLEOTIDE PRIMER, FIG. 20

( x i ) SEQUENCE DESCRIPTION: SEQ ID NO:2:

CGATGGCACA CAGCGAGCCC AC  22

( 2 ) INFORMATION FOR SEQ ID NO:3:

( i ) SEQUENCE CHARACTERISTICS:
        ( A ) LENGTH: 139 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: CLONE AG8, FIG. 21

( x i ) SEQUENCE DESCRIPTION: SEQ ID NO:3:

CAGGCCTCCA TGAGGGAGCT GGGGCTGCTC ATCTTCTTCC TCTTCATCGG GGTCATCCTC  60
TTCTCCAGTG CCGTCTACTT CGCAGAGGCT GACAACCAGG GAACCCATTT CTCTAGCATC  120
CCTGACGCCT TCTGGTGGG  139

( 2 ) INFORMATION FOR SEQ ID NO:4:

( i ) SEQUENCE CHARACTERISTICS:
        ( A ) LENGTH: 139 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: HUMAN VOLTAGE-GATED POTASSIUM CHANNEL K1, FIG. 21

( x i ) SEQUENCE DESCRIPTION: SEQ ID NO:4:

CAGGCCTCCA TGAGGGAGCT GGGGCTGCTC ATCTTCTTCC TCTTCATCGG GGTCATCCTC  60
TTCTCCAGTG CCGTCTACTT CGCAGAGGCT GACAACCAGG GAACCCATTT CTCTAGCATC  120
CCTGACGCCT TCTGGTGGG  139